US008882552B2

(12) United States Patent
Lambert

(10) Patent No.: US 8,882,552 B2
(45) Date of Patent: Nov. 11, 2014

(54) BIOPHYSICAL GEOENGINEERING COMPOSITIONS AND METHODS

(71) Applicant: Kal Karel Lambert, Hammond, OR (US)

(72) Inventor: Kal Karel Lambert, Hammond, OR (US)

(*) Notice: Subject to any disclaimer, the term of this patent is extended or adjusted under 35 U.S.C. 154(b) by 0 days.

(21) Appl. No.: 13/969,592

(22) Filed: Aug. 18, 2013

(65) Prior Publication Data
US 2013/0339216 A1 Dec. 19, 2013

Related U.S. Application Data

(63) Continuation-in-part of application No. 13/225,885, filed on Sep. 6, 2011, now Pat. No. 8,535,107, which is a continuation-in-part of application No. 12/463,409, filed on May 10, 2009, now Pat. No. 8,033,879, which is a continuation-in-part of application No. 12/404,691, filed on Mar. 16, 2009, now abandoned, which is a continuation-in-part of application No. 12/345,661, filed on Dec. 26, 2008, now abandoned.

(60) Provisional application No. 61/009,414, filed on Dec. 29, 2007.

(51) Int. Cl.
B63B 39/10 (2006.01)
B63B 22/00 (2006.01)
G06Q 40/04 (2012.01)
A01G 15/00 (2006.01)
C12N 1/12 (2006.01)
B01D 53/84 (2006.01)

(52) U.S. Cl.
CPC ............... *G06Q 40/04* (2013.01); *A01G 15/00* (2013.01); *C12N 1/12* (2013.01); *B01D 53/84* (2013.01); *B01D 2259/4558* (2013.01)
USPC ................................. 441/1; 114/234

(58) Field of Classification Search
USPC ...................... 114/232, 234; 441/1
IPC ......................................................... B63B 22/00
See application file for complete search history.

(56) References Cited

U.S. PATENT DOCUMENTS

| | | | | | |
|---|---|---|---|---|---|
| 6,056,919 | A | * | 5/2000 | Markels, Jr. | 422/40 |
| 6,868,361 | B2 | * | 3/2005 | Desa et al. | 702/156 |
| 8,033,879 | B2 | * | 10/2011 | Lambert | 441/1 |
| 8,535,107 | B2 | * | 9/2013 | Lambert | 441/1 |
| 2005/0118122 | A1 | * | 6/2005 | Simon et al. | 424/63 |
| 2006/0121166 | A1 | * | 6/2006 | Jeckle | 426/395 |

* cited by examiner

Primary Examiner — Stephen Avila
(74) Attorney, Agent, or Firm — K Karel Lambert; Lambert Patent Services LLC

(57) ABSTRACT

Described here are compositions, methods and apparatus for biological and physical geoengineering. A vertical spar buoy or spar buoy network is provided. The buoys or array of buoys are designed to resist wave motion while supporting an analytical platform at a depth such that particulate flux of fixed carbon is indicative of sequestration in the ocean's depths for one hundred years or more. Sedimentary deadfall through the 100-Year Horizon is measured to validate the flux of fixed carbon. Issuance of validated carbon sequestration certificates and monetization and trading of those certificates are described. Also provided are compositions and methods for increasing bioactive surface area and nutrient levels so as to promote carbon sequestration. Regeneration of carbon dioxide in the mesopelagic water column is reduced by providing complex habitat in the photic zone, thus ensuring higher complexity of trophic levels and sedimentary deadfall having larger particulate size.

19 Claims, 26 Drawing Sheets

Fig. 15A Fig. 15B
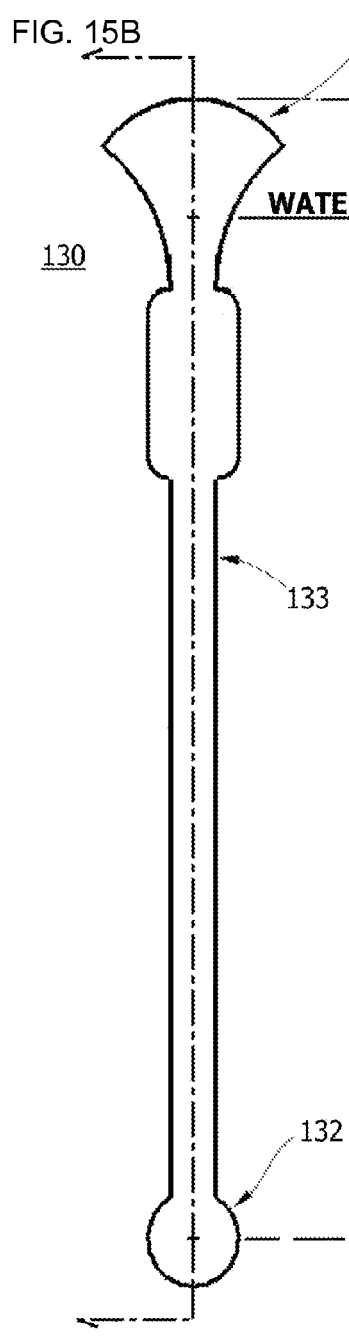
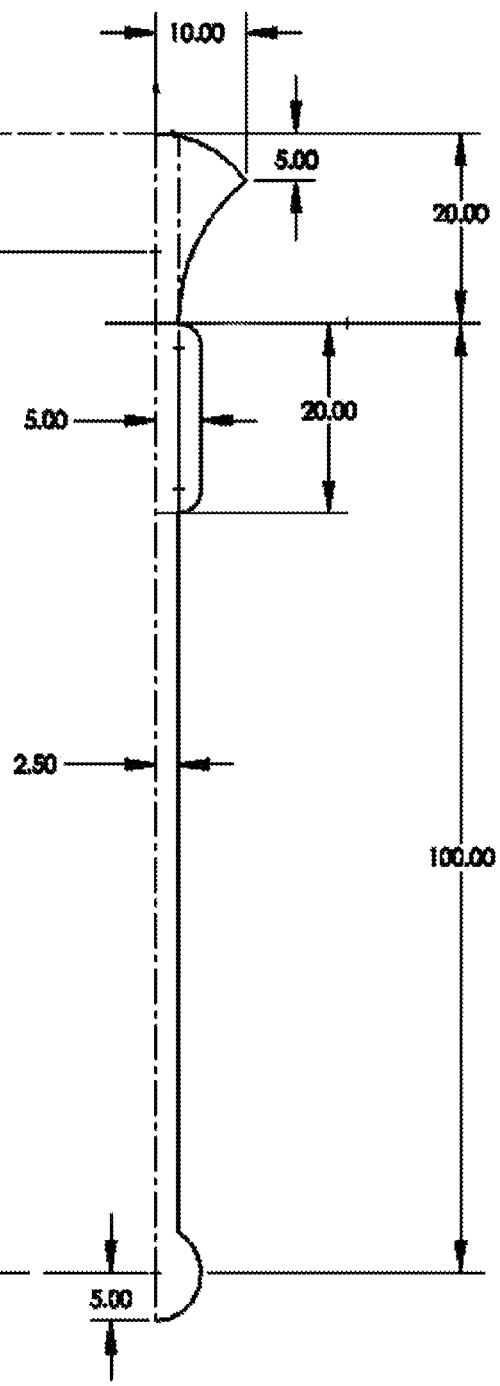

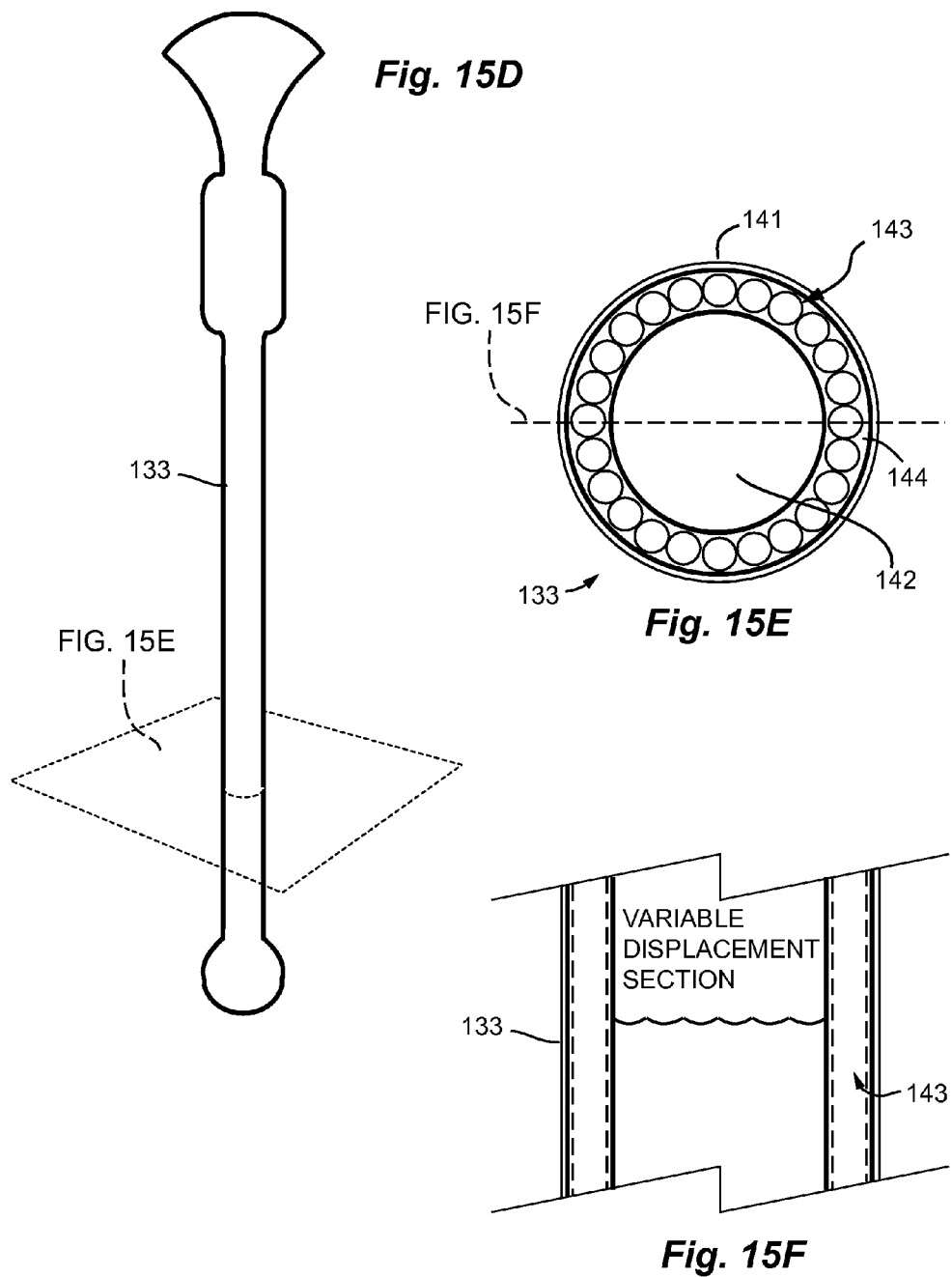

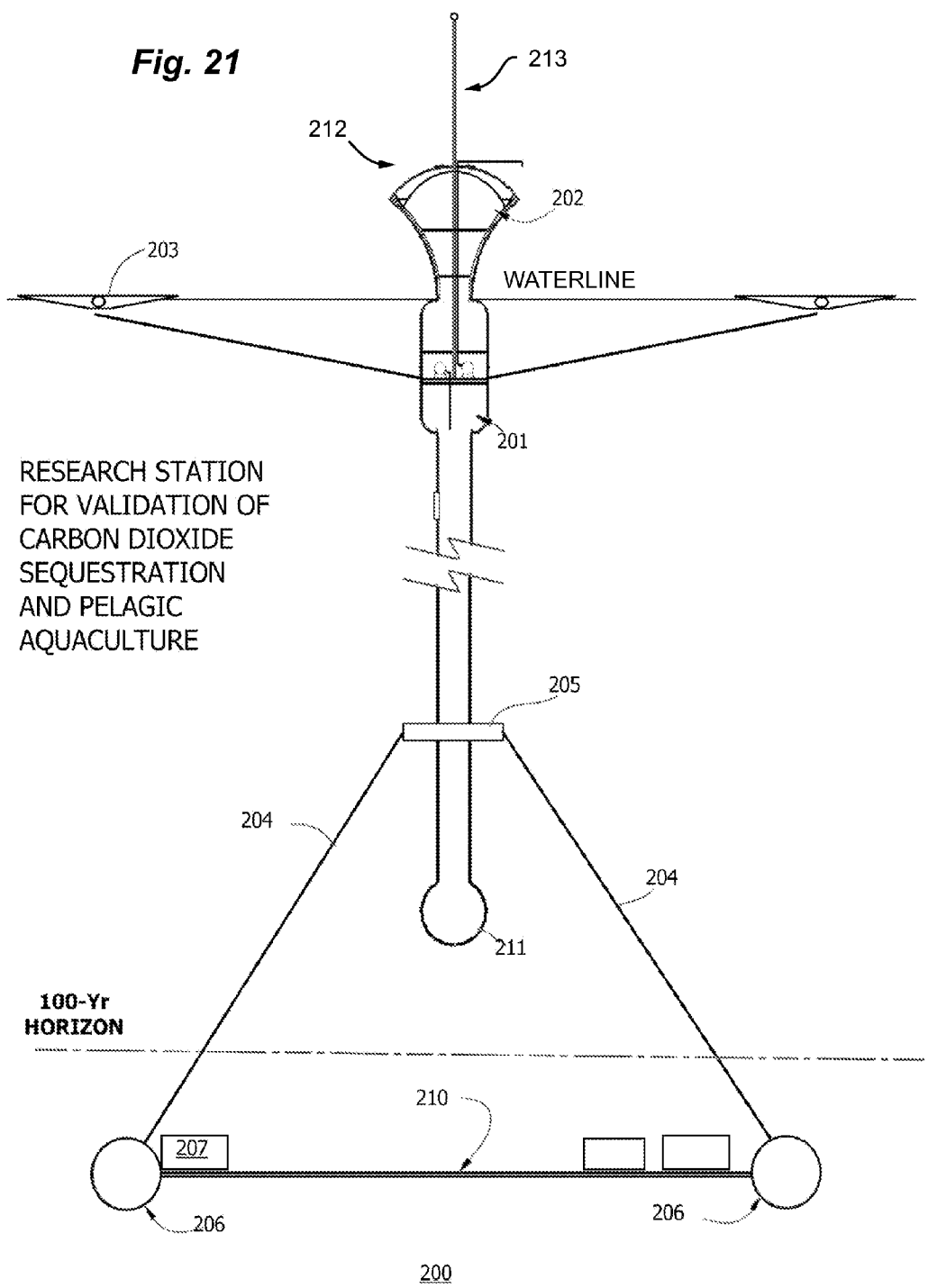

*Fig. 22*

TERRAFORMING FOR CO2 REMEDIATION

BUILDING NETWORK OR ARRAY OF SPAR BUOYS DEFINING A BOUNDED SURFACE AREA OF AN OCEAN;

DISPERSING A BUOYANT INORGANIC COMPOSITION WITHIN THE BOUNDARY AREA AT A PARTIAL FILL FACTOR, THE COMPOSITION HAVING A TOPOLOGY WITH MICROSCOPIC AND MACROSCOPIC NICHES;

SUSPENDING FROM THE NETWORK OR ARRAY OF SPAR BUOYS A SPACE FRAME DEFINING A 100 YEAR HORIZON DEPTH;

MOUNTING AN INSTRUMENT PACKAGE ON THE SPACE FRAME FOR MEASURING SEDIMENTARY DEADFALL THROUGH THE 100 YEAR HORIZON;

MEASURING AND INTEGRATING FLUX OF SEQUESTERED CARBON PER UNIT TIME;

VALIDATING FLUX OF SEQUESTERED CARBON CROSSING 100 YEAR HORIZON; AND

ISSUING ONE OR MORE MONETIZABLE OR TRADABLE CARBON SEQUESTRATION CERTIFICATES HAVING A DENOMINATION BASED ON VALIDATED CARBON FLUX.

CONTINUE FOR EFFECT

*Fig. 26*

CONTINUOUS TERRAFORMING FOR CO2 REMEDIATION

BUILDING A NETWORK OR ARRAY OF SPAR BUOYS HAVING A RENEWABLE ENERGY SOURCE;

PROVIDING HABITAT AND/OR SELECTED NUTRIENTS WITHIN A BOUNDARY DEFINED BY THE THE NETWORK OR ARRAY;

PUMPING DEEP WATER UP SO AS TO ADMIX WITH NUTRIENT-DEPLETED SURFACE WATER;

AT DEPTH, MOUNTING AN INSTRUMENT PACKAGE FOR MEASURING SEDIMENTARY DEADFALL THROUGH THE 100 YEAR HORIZON;

MEASURING AND INTEGRATING AN ACCELERATION IN THE FLUX OF SEQUESTERED CARBON CROSSING THE 100 YEAR HORIZON PER UNIT TIME; AND,

ISSUING ONE OR MORE MONETIZABLE OR TRADABLE CARBON SEQUESTRATION CERTIFICATES HAVING A DENOMINATION BASED ON A VALIDATED INCREASE IN SEQUESTERED CARBON FLUX.

CONTINUING FOR EFFECT

BIOPHYSICAL GEOENGINEERING COMPOSITIONS AND METHODS

CROSS-REFERENCES TO RELATED PATENT DOCUMENTS

This application is a continuation in part, and claims the benefit of priority under 35 U.S.C. 120, of U.S. patent application Ser. No. 13/225,885, filed on 6 Sep. 2011, now U.S. Pat. No. 8,535,107, which is a continuation-in-part claiming the benefit of priority under 35 U.S.C. §120, of U.S. patent application Ser. No. 12/463,409 filed on May 10, 2009, now U.S. Pat. No. 8,033,879, which is a continuation-in-part of U.S. patent Ser. No. 12/404,691 filed on Mar. 16, 2009, now abandoned, which is a continuation-in-part claiming benefit of priority under 35 U.S.C. §120 from U.S. patent application Ser. No. 12/345,661 filed Dec. 29, 2008, now abandoned, which is a non-provisional application claiming benefit of priority under 35 U.S.C. §119(e) from U.S. Provisional Patent Application Ser. No. 61/009,414, filed Dec. 29, 2007; all said priority documents are incorporated herein in entirety by reference.

FIELD OF THE INVENTION

Embodiments of the invention as disclosed here relate to apparatus and methods for increasing marine productivity and marine deep ocean carbon sequestration. Also described are carbon sequestration certificates based on validated removal of carbon dioxide from the atmosphere by an enhanced biological pump.

INTRODUCTION

Solar radiation striking the Earth's disk is in equilibrium with energy re-radiated as reflected light or as heat at longer wavelengths. The atmosphere traps a great deal of infrared radiation, warming the surface significantly above the black body temperature of the planet, which is a chilly $-20°$ C. However, there can be too much of a good thing. As a result of accumulation of greenhouse gases, we have now entered a period of excess warming. Reversing global warming requires re-adjusting the greenhouse gas composition of the atmosphere—and/or also proportionately removing energy from the planetary heat engine—until the current sharp upturn in global surface temperature is brought to a halt.

The atmosphere is bidirectionally transparent to light in certain ranges of wavelengths. These ranges are known of as "atmospheric windows". Reflected light is thus one means to remove incoming solar energy from the planetary heat balance. Albedo is a measure of the reflectivity of the planetary surface, and can be measured with satellite-mounted pyrometers. Changes in albedo result in very large scale net changes in the heat energy balance of the planet, and over short time frames. For example, IPCC models are now incorporating the area of solar panel installation worldwide—as an added heat source—into the assumptions for projected global warming, because conventional solar panels have very low albedo and re-radiate about 90% of incident light energy as black body radiation that is trapped by the atmosphere. Decreases in albedo are associated with planetary warming.

Conversely, increases in planetary albedo are expected to result in global cooling. Deliberate reconfiguration of planetary albedo is not without possible benefit, as evidenced by proposals under the aegis of the National Academy of Sciences to seed the high stratosphere with reflective particles.

A second means to alter planetary warming is to modify the gas composition. Adding greenhouse gases such as carbon dioxide increase global mean temperatures; removing or sequestering them will result in global cooling, ideally to the Goldilocks temperature most conducive to life as we know it.

The problem is how to achieve a maximal benefit without causing harm. The work here begins with the question as to whether there is merit in "down to earth" geoengineering works to modify albedo and/or carbon dioxide levels in the atmosphere, and whether this can be done both economically (socio-ecological benefits exceeding direct and incidental costs of resource allocation) and safely. The answer is "yes" on both counts, as will be apparent on consideration of the following.

BACKGROUND TO THE PROBLEM

Direct climate intervention strategies on Earth (geoengineering, or more colloquially "terraforming") have not generally been viewed as a benefit, but more as a hazard. In light of current trends in climatology, it may be necessary to rethink these reservations. For starters, unintended geoengineering is well underway on a massive scale, and there is convincing evidence of anthropogenic causality for climate change. Current anthropogenic release of carbon dioxide from fossil fuels and cement production is about 7 GtC/yr (7 metric gigatons as carbon) annually and may reach 12 GtC/yr by 2050, with probable net doubling of atmospheric $CO_2$ in the lifetime of our children. This inadvertent geoengineering was inevitable given the greenhouse forcing we have caused by fossil fuel combustion, and the only subject of debate (FIG. 1) is the intensity of its future impact. Among the complications we are seeing today: overpopulation, violence, economic collapse, poverty, deforestation and desertification.

The scale of the problem is difficult to grasp. Future atmospheric $CO_2$ concentrations in the year 2100 are projected by the IPCC to be in the range of 540 to 970 ppm, compared to only 370 ppm in the year 2000, 400 ppm in the year 2013, and less than 280 ppm before the industrial revolution. Perhaps more impressive than concentration are the pool sizes themselves. Current atmospheric total $CO_2$ is about 750 $GtCO_2$ as mass, a doubling of the 360 $GtCO_2$ in the atmosphere less than 200 years ago.

Also of interest are the current flux rates. Fossil fuel export to the atmosphere is more than 6 GtC per year at present and is increasing sharply. Of this, about net 2 GtC is being absorbed in the oceans annually (about 30% of the carbon dioxide emissions from fossil fuel combustion). Since 1800, the ocean has absorbed about 135 GtC carbon dioxide; and has become correspondingly more acidic. Interestingly, higher rates of increase in atmospheric $CO_2$ tend to occur in El Niño years, as would be consistent with a Henry's Constant effect on the atmospheric/marine solubilized carbonate species equilibrium. Currently, the pool size of inorganic carbon in the mesopelagic water column is about 5.4 GtC, ensuring that atmospheric $CO_2$ will continue to rise for centuries, even if fossil fuel combustion is stopped tomorrow.

In addition, there is a high risk of positive feedback, the so-called "runaway" greenhouse effect. Total $CO_2$ pools incipiently releasable into the atmosphere (from long term sequestered stores in permafrost and methane hydrate deposits) as carbon are measurable in Teratons (i.e. exceeding $10^{12}$ tons as carbon). Because these pools are orders of magnitude larger than the existing total atmospheric pool, it should be clear that activities that could cause their release into the atmosphere are likely to result in mass extinctions at all levels of the food chain. The trigger for melting permafrost and release of methane hydrate pools held in place by the ice caps may have already been pulled, but in light of the magnitude of the potential $CO_2$ release, it seems eminently sensible to act quickly to attempt to quickly reverse our present course.

Yes, we are responsible for these transformations. Total human energy use is measurable in exaJoules (and is about 1000 EJ or $10^{21}$ J annually). Of that, about 40% (400 EJ) is currently derived from fossil fuel consumption. Conceptually, a burning candle can be imagined as equivalent to 0.8 J/s, so that the rate of human energy consumption is equivalent to perhaps 50 trillion candles burning simultaneously, or 6,000 candles for every person on the planet, all burning around the clock. More conventionally, the number is about 10-20 MWhr/capita in developed countries, or potentially $1$-$2 \times 10^{10}$ MWhr for the global population, assuming a peak population of 9 or 10 billion and a "Western" standard of living. Notwithstanding the population overshoot, clearly the practice of burning anything to meet this kind of energy load is unsustainable, and perhaps the standard of living itself is unsustainable given the population base. Geoengineering is not a small thing to have done by accident, and it will not be a small thing to undo.

Therefore, there is an urgent need to re-engineer the planetary economy, both by restructuring industry, feedstocks, carbon footprints, and the like, but also by ameliorating ongoing damage to our shared "commons", the atmosphere and the oceans. This constitutes remedial terraforming, but here is termed "rational geoengineering" to better differentiate the science from the science fiction.

Rational approaches to geoengineering can be divided into two categories: biological and physical. Among the biological approaches are: carbon sequestration by marine fertilization and terrestrial or marine silviculture. Among the physical approaches are: injection of microparticulate reflectors into the stratosphere (as per the "Pinatubo Effect"); extraterrestrial solar parasols; carbon dioxide storage in geological formations (generally as carbonates); carbon dioxide storage in deep sea lakes (as liquified $CO_2$), and the like. The scale of any such project can be judged by comparison with more conventional alternatives: for example, an immediate roll-out of 6,700 new nuclear power plants (assuming 6.8 GWhr per plant, sufficient enriched uranium, and no waste in electrical distribution) would be required to zero out power consumption derived from fossil fuel alone (fossil fuel consumption is currently about 400 EJ or $4.6 \times 10^7$ GWhr annually and rising). At current cost of US$ 10B/plant, construction of an adequate number of nuclear power plants would amount to US$ 65 Trillion in present dollars and would take decades. Currently, less than 500 nuclear power plants are installed worldwide.

There are alternatives. Solar power is dependent on solar insolation, an essentially free energy source which averages out to about 160 W/m² (160 J/s/m²) over the surface of the planet. Again taking 400 EJ as the target, replacing today's fossil fuel combustion with photovoltaic cells operating at 10% efficiency would require a solar panel array (or combined equivalent) the size of Venezuela, more than 400,000 km² if placed equatorially. Also a factor is the heat required for manufacture, such as by the Czochralski process, and periodic replacement of solar panels, capacity for which is practically nonexistent considering the scale. Current solar cell designs radiate heat as black bodies, emitting a great deal of waste heat, so that on the scale envisaged, heat emission from the required surface area of solar cells is likely to reach 2000 EJ annually (assuming 50% conversion to "new" heat), five times the current heat generated from fossil fuel combustion! Like water, conventional solar cells have the albedo of black asphalt. Taking solar insolation at the terrestrial surface as about 45 PW, the incidental heat pollution of the solar panels would be 4% of the overall global surface heat budget. Net flux of heat IN will exceed net heat OUT until a new global surface temperature at equilibrium is reached. The effect would be analogous to removing the high-albedo icesheet from Greenland and replacing it with a low-albedo asphalt surface, but positioned equatorially.

Measurements in support of a dramatic climate forcing by terrestrial albedo are readily found. In a widely cited paper by Palle (2004, Science 304:1299-1301), an observed decrease in global albedo of 0.02 was associated with an increased global heat budget of 6.8 W/m², a highly significant increase climatologically. Much of the decrease in global albedo is the result of anthropogenic changes in land use, vegetation, burning of forests, and deposition of soot upon snow. Installation of solar panels has been added to that list.

Currently, installed wind power on line is about 157 Million MWHr or 0.34% of global demand. The Picken's plan in Texas would add 4,000 MWHr to this total, a rather small amount expected to cost $10 billion. Within a few decades, because of the constancy of wind in Patagonia, more than 1.3 Trillion MWHr per year could be installed, or about 3.2% of global demand. But these areas of sustained strong wind are unusual and the estimates do not factor power losses through an electrical distribution grid or losses in a conversion process to liquid fuel for export.

Arable land required for biomass energy capture and conversion is estimated at anywhere from 13,700 to 32,000 km²/EJ. To capture the equivalent of 400 EJ, perhaps $8 \times 10^6$ km² must be converted to cropland, an area the size of Australia, or about 5% of the earth's land mass. This does not factor in the overhead energy costs of farming, which should perhaps double the area needed. Currently, about $1.3 \times 10^6$ km² is under cultivation in the US for food crops. So again, the undertaking is beyond enormous—energy crops cannot simply replace food crops worldwide without major sociopolitical consequences. The irreplaceable and unsustainable bounty of readily available fossil fuels simply cannot be overstated.

Population extinction by economic pressure has also been considered as a solution to the climate dilemma we face, but the social dislocations of such a program pose considerable risks to those who would execute it, no matter what walls are constructed. In an article titled, "Guns beat Green", writer Naomi Kline, writing in the December 2007 *The Nation*, shows that market investments favoring a fortress mentality, private security for the wealthy and weapons at the borders, surpassed new investments in sustainable energy technologies. Weapons and security technologies received 6 Billion $US in venture capital in 2007 whereas green technologies received only 4.3 Billion, and the gap has been widening. Peak oil is on the near horizon, consumers are increasingly turning to natural gas, and the consensus in the stock market seems to be that those with the guns will consume the last gallon of gasoline, the last cubic foot of natural gas, and the last bucket of coal! Clearly the betting money is on economic Darwinism to solve the problem of climate change. But can we truly sustain a Maginot Line or Demilitarized Zone in the face of new and greater waves of hungry illegal immigrants at our borders? Can we fortify our communities and not be impacted by a worldwide collapse of democratic values, commodities, currencies, and access to markets such as we are now seeing?

Clearly, no single program is feasible at the scale required. Conservation efforts, for example business metrics based on "carbon footprint", are laudible but not yet up to the Draconian task required to eliminate 400 EJ from the annual global energy budget. Although comforting, and in the short term profitable to some, recent innovations in carbon trading are far from meaningful net reductions, and are in fact a sort of shell game that in all likelihood attempts to obfuscate the scope of the problem in the name of corporate public relations.

Alternatives to the handling of fossil fuels have also been proposed. What is euphemistically termed "clean coal" technology, for example, proposes to inject by-product $CO_2$ from coal gasification or power production into sub-terrestrial strata such as depleted oil fields. While this sounds attractive, the changes in albedo and atmospheric $CO_2$ resulting from use of coal are more likely than not to result in a net planetary heat gain and is unsustainable.

Finally, business as usual is clearly not an option, such a course posing unacceptable hazards and burdens for future generations. Part of the problem relates to the reluctance of human societies to put a value on the commons, for example a tax or "debit" for use of the atmosphere as a "sink" for $CO_2$ (and heat) generated by an industrial process. Heat can also be considered a waste, and while it may be convenient for the polluter to dump it into the atmosphere or an ocean, there may be a social cost or lost benefit not currently taken into account in our economic balance sheets. Exacting payment for heat disposal would be difficult however, excepting contracting to a Maxwell's Demon, unless there was a way to actively transport net heat from the planet and "credits" for that ameliorative process could be issued and traded. As discussed here, such a system is not impossible, but requires engineering deliberate increases in terrestrial albedo, and in the short term, reductions in atmospheric $CO_2$.

Can/will the greenhouse effect be slowed down? FIG. 1 suggests the current trend in global mean temperature, which is tied closely to $CO_2$ release into the atmosphere. Note that 2100 does not bring a plateau in the relentless rise in global mean temperature that started in the late $20^{th}$ century, and we are again forced to ask whether our lifestyle presages retreat of temperate climate zones poleward, deforestation by fire and insect population explosions, and mass extinctions.

In addition to combustion of fossil fuels, other sources of greenhouse gases must be considered. Pre-industrially, deforestation accounted for about 75% of the total annual increase in atmospheric carbon dioxide, but is now only about 20%, having been swamped by rising fossil fuel combustion. Globally, the four activities responsible for most $CO_2$ emissions are: 1) fossil fuel combustion, 2) deforestation, 3) agriculture and 4) manufacture of Portland cement.

Conversion of native ecosystems to cropland or pasture continues to be associated with both soil deterioration and release from soil humus of up to perhaps 1.5 Tt of sequestered carbon, an ongoing process. Remaining fossil fuel reserves, importantly including coal, are estimated at over 5 Tt C (18 Tt $CO_2$), and most of this is being developed or evaluated for "exploitation", perhaps understandably given the market premium placed on the value of gasoline, which is only likely to rise. Not surprisingly then, use of fossil fuel reserves seems to be accelerating. Psychology is a critical factor confounding the hard science of global warming, and there will be a need for temporary relief, a cooling off period, so that the reality of the situation can be fully assimilated and a sober commitment to a sustainable future can be engendered.

There had been an expectation for some time that a negative feedback mechanism in global climate would emerge, a sort of "Gaia-effect", perhaps in the form of increased oceanic albedo through cloud condensation nucleii as proposed by Robert Charlson of the University of Washington in 1987 (Nature 326:655-61). However, we can also expect the opposite—positive feedback effects. One such example is found in the expected effects of a meltdown of the West Antarctic ice sheet. Accounting for the rebound of the Earth's crust following relief from the weight of the ice sheet, and resulting shift in polar axis of rotation, the predicted 5 m sea level rise is expected to be even higher, perhaps 6.3 m, in the northern hemisphere, where the bulk of the continents are located (Mitrovica, J X et al. 2009. The sea level fingerprint of West Antarctic collapse. Science 323:753). Increased ocean surface area resulting from continental flooding can be expected to dramatically reduce global albedo over large areas, in aggregate reducing reflected heat and increasing the temperature "set point" of the planet. A similar positive-feedback potential of carbon release from permafrost and methane hydrates (pool size >1 TtC) has already been mentioned. No deux-ex-machina to cool the planet can be relied on; it appears we are on our own.

Divine intervention aside, an exponential reverse J-curve in economic activity and population is the more likely negative feedback we can expect in the short term. Deceases in human activity have been associated with periods of relief. For example, changes in agriculture and silviculture practice across northern Asia following the dissolution of the Soviet Union resulted in measurable decreases in radiative forcing due to greenhouse gas heating (i.e., decreases in livestock husbandry resulting in decreased production of methane) and increases in forest carbon dioxide sinks (by decreases in timber harvesting). Ruddiman has proposed a related argument associating cooling trends observed following first contact of Europeans and Native Americans. Similarly, slowing of global economic activity due to the 2008-2013 banking crisis will likely be shown to have reduced carbon dioxide output. At the very least, a decrease in carbon dioxide output and global warming superimposed on a downturn in human economic activity will relieve any lingering doubts in the minds of planners that greenhouse warming is anthropogenic at its belly button.

Thus by the process of elimination of alternatives recited here, geoengineering must be seriously considered as part of any comprehensive effort to solve the problem—absent any compelling argument to the contrary. Two arguments against rational geoengineering are commonly made. First that the ecological risks are unacceptable. Second that any ameliorative action taken would ease the pressure to make the hard decisions needed to develop a sustainable energy economy. Both these arguments will likely wilt when and if global warming enters a "runaway" phase. Arguments about ecological risk must seem hypocritical even now given the reckless behaviors that have produced the crisis. In short, it seems inevitable that resistance to rational terraforming will evaporate when temperatures or sea level spikes sharply. Therefore the "roll-out" of any terraforming device must have a short lead time and quickly become effective. It is reasonable to want to prepare for this while organized economic activity on a global scale is still possible. Preliminary studies undertaken at this time, undertaken to ensure that an effective response will be available when the political urgency becomes compelling, seem entirely defensible and in fact of the highest priority.

A worst case acute meltdown and global temperature spike would likely be marked by a sharp upturn in fossil fuel combustion emissions and then a generational declining standard of living: simply because the costs of adapting to planetary ecosystem disruption will be so high. More optimistically, the crisis could spike and then correct itself through adoption of new technologies over several decades, peaking sometime between 2020 and 2050—maybe. Optimally, a geoengineering device and method for amelioration of the global heat budget and greenhouse effect might be required for a few years or a decade to blunt peak emissions, following which we ultimately make more sustainable choices for powering a quality of life for all. Thus a geoengineering apparatus or process would thus simply be a means for gaining the time needed for committed change, and conveniently, would then dissipate and vanish without further intervention, or could be turned off or redirected. In this view, rational geoengineering is seen not as an artifice to evade, but rather as a potential borrowing of time to face an incipient crisis and make the necessary changes.

One geoengineering proposal has emerged as feasible, economical, and likely to be effective, albeit with uncertain collateral consequences. In the Pinatubo eruption, approximately 10 Mt sulfur as a $SO_2$-rich aerosol was transported to stratospheric levels above 30 km. The plume, covering a band of some 125,000 $km^2$, reduced global insolation, when measured 6 months later, by about 4.5 $W/m^2$ (or global mean average of about 3%). Mean global temperature dropped by about 0.5 degrees Celsius (0.9° F.) for over a year following the eruption. A similar impact was seen after the El Chichon eruption of 1982 and after Tambora, another stratovolcano, in 1816, which was followed by a "year without a summer" and crop failures in Europe. Nobel Prize winner Paul Crutzen has published a thumbnail feasibility study for NASA-assisted injection of nanoparticles into the stratosphere, offering to mimic the beneficial cooling effect that follows stratovolcanos. (see www.deas.harvard.edu/climate/pdf/2006/Crutzen2006.pdf). In short, a significant increase in planetary albedo can be achieved by any party possessing the capacity to lift 100 Mt of volcanic ash into the stratosphere, purportedly a relatively cheap proposition. The "Pinatubo Effect" as it is now called, was equivalent to 0.75 $W/m^2$ in reduced insolation. However, sulfur dioxide attacks ozone and precipitates as acid rain. A better choice of aerosol might be microparticulate olivine, mica, or diatomaceous earth, which are available in abundance. But doubts as to the feasibility and safety persist.

Some work toward marine geoengineering was initiated on a small scale as early as 1993, and the results have been confirmed in numerous subsequent studies. As set forth in detail at www.palomar.edu/oceanography/iron.htm (accessed 30 Jan. 2007), the IronEx I research vessel Columbus Iselin set out to sea in 1993 fitted with a portable laboratory and loaded with 21 barrels of blue-green iron granules (about 0.5 t of ferric sulfate). The mineral was dissolved in seawater at the test site and dispersed in a location SW of the Galopagos Islands. Application resulted in increase of iron from about 20-50 pM to about 1-2 nM and a three-fold increase in phytoplankton (measured as chlorophyll) in the treated area. The biological enrichment resulted in transient sequestration of about 300 t carbon dioxide over a two week period but was complicated by unexpected surface stratification. This experiment generated a tremendous debate and was repeated in 1995, with yet better results, stimulating a 30× increase in surface chlorophyll, principally in the form of diatoms, but also higher trophic levels, as had been predicted. An estimated 9,100 t of carbon dioxide was drawn down. Encouragingly, follow up work has not demonstrated significant collateral production of NOX or methane.

The effort was originated in 1986 by John Martin of Moss Landing Marine Laboratories, and was first disclosed in response to a presentation by Bruce Frost of the University of Washington, who had noted that some ocean areas were unexpectedly phytoplankton poor (the "high-nitrate/low chlorophyll" oceans), for example the Pacific equatorial belt extending east from Irian Jaya to Peru and the roaring 40's, the belt of water surrounding Antarctica. Martin had suggested that biological productivity was limited by iron availability, and that iron fertilization would result in a phytoplankton bloom and could be used as a means to reduce the greenhouse effect (which was already well understood in scientific circles by the 1980's) by sequestering carbon dioxide. See for example, Martin et al. 1990. Glacial-interglacial $CO_2$ change: The iron hypothesis. Paleoceanography 5:1-13 and discussions [www.palomar.edu/oceanography/iron.htm] of the period. Use of marine fertilization with iron to stimulate marine productivity and sequester $CO_2$ is thus not a novel concept and a first full, clear and definite conception was articulated in the mid-1980s.

In the second Iron-Ex expedition, in 1996, headed by Kenneth Coale, it was noted that the redox state of the inorganic iron was important, ferric iron precipitating rapidly as the hydroxide and exiting the photic zone. Nonetheless, a dense and somewhat anoxic phytoplankton bloom was observed and documented.

Other experiments of this same kind have since been published (see Tsuda A et al. 2003. A mesoscale iron enrichment in the western subarctic Pacific induces a large centric diatom bloom. Science 3009:58-61; Markels and Barber. 2001. Sequestration of $CO_2$ by ocean fertilization. Poster Presentation for NETL Conference on Carbon Sequestration; Boyd P W et al. 2000. A mesoscale phytoplankton bloom in the polar Southern Ocean stimulated by iron fertilization. Nature. 407: 695-702; Coale K H et al. 2004. Southern Ocean iron enrichment experiment: carbon cycling in high- and low-Si waters. Science 304:408-14; Boyd P W et al. 2004. The decline and fate of an iron-induced subarctic phytoplankton bloom. Nature 428:549-53). A total of 12 experiments were recently reviewed by Boyd (Boyd P W et al. 2007. Mesoscale iron enrichment experiments 1993-2005: synthesis and future directions. Science 315:612-7). A newsworthy update was recently published in Science (318:1368-70, 2008).

Patent literature has also accumulated, beginning with a 28 Apr. 1994 filing by Markels (U.S. Pat. No. 5,433,173), which claimed a method for first measuring nutrients in seawater, of then adding any missing nutrients to the seawater, and finally harvesting the increased production as seafood. Use of a "float material" such as rice hulls, wheat chaff, ground corn cobs [and] peanut hulls was proposed as a form of fertilizer that would dissolve in the surface over a period of days, or perhaps as long as a week. The detailed description involved shipboard pumping of a liquid fertilizer composed primarily of iron with some phosphates and nitrates, and disclosed "that almost certainly algae will grow". It can be said that John Martin unequivocally articulated that same assertion almost a decade earlier. Markels' patent was awarded with narrow claims.

This was followed by U.S. Pat. No. 5,535,701, which cited one of the Martin papers (Martin et al. 1994. Testing the iron hypothesis in ecosystems of the equatorial Pacific Ocean. Nature 371:123-129). In the second filing, the method was supplemented by further providing a nitrogen-fixing organism with the fertilizer. As examples of compositions for such use of fertilizers, starch mixtures with iron were suggested. Compositions were again not claimed.

In U.S. Pat. No. 5,967,087, Markels claimed a method for increasing seafood production, where the fertilizer contains iron in a chelated form so that the iron does not precipitate from the photic zone as hydroxides. Compositions for the method were disclosed. The compositions included binders such as plastic, wax, or starch to provide timed release over two weeks of the fertilizer, and a plastic pellet matrix compounded to float by attaching the fertilizing matrix to a float material such as glass bubbles, plastic foam, or by introducing gas bubbles into the fertilizer pellets during manufacture. The matrix selected for attaching the fertilizing elements to the float element or for introducing gas bubbles into the fertilizer pellets was taught to be a plastic matrix, or optionally a wax (Col 4 lines 48-65). Again the timed release matrix disclosed was selected to dissolve in two weeks or less, and in subsequent disclosures, pulse fertilization at intervals greater than 30 days was reported as preferable.

In 2000 and 2002, two US patents issued to Markels claiming methods for sequestering carbon dioxide by ocean fertilization. In U.S. Pat. No. 6,056,919 the steps of the claimed method involve testing to identify a missing nutrient, applying a fertilizer to supply the nutrient, limiting the bloom by applying the fertilizer in pulses, and measuring the amount of carbon dioxide sequestered. Pulse application at intervals of greater than 30 days (see independent claims 1 and 15) was taught to limit anoxia in the phytoplankton blooms. It is known that micrograzing and eutrophication result in lessened carbon sequestration.

In U.S. Pat. No. 6,440,367, methods of applying iron chelates to the ocean were claimed for sequestration of carbon dioxide. Disclosed was an iron:lignin chelate. In this case, and all such related cases, the teachings teach away from the use of the less expensive insoluble mineral forms, which would be expected to precipitate if mixed into the ocean—an unsolved problem.

US Patent Appl. 2002/0023593 relates again to methods of increasing seafood production. Claims 1, 10 and 14 summarize the relevant teachings as to compositions: [a method wherein] first, iron is to be supplied as a chelate, and secondly, "said second fertilizer is in the form of pellets, and said pellets comprise a float material selected from gas bubbles and/or low density materials, and said pellets further comprise a binder selected from plastic, wax, high molecular weight starch, or a combination thereof". Any such composition consists of an organic binder, a float material, and an iron chelate, but note that the claims relate strictly to methods, and that in all the claims in this series, the steps are always to measure the nutrient concentrations in seawater, to determine the limiting nutrient, and then to supply that nutrient, the substance of what John Martin had proposed for iron-poor oceans. A method in which the limiting nutrient is not measured is not claimed, although most scientists would be reluctant not to collect baseline data before undertaking iron enrichment as a matter of ordinary skill in the art. Also not conceived was a method in which non-limiting nutrients were added, for example so as to favor certain communities over others.

As for compositions, the methods of the prior art teach solubilized minerals, chelates, and a narrow genus of pellet matrices selected from the list of organic chemicals consisting of plastic, wax, and starch. All such pellets contain an organic binder. However, selection of an organic matrix is problematic in that the named materials are responsible for very high levels of biological oxygen demand, starch for example, thus promoting the growth of heterotrophs, particularly bacteria not native to the pelagic ocean, which will certainly exacerbate oxygen depletion in the underlying water and reduce carbon sequestration by resolubilizing any carbon dioxide fixed by primary producers. Plastic materials are also a major pollutant in the world's oceans and typically contain carcinogenic plasticizers. Wax is not expected to form monodisperse sustained-release pellets absent a surfactant and is difficult to handle. Other objections to the selections taught by Markels could be elaborated here. Organic binders will likely have a highly negative effect on ocean surface chemistry by disintegrating into short chain oils and organic polymers, and thus displacing native surfactants, chelators, siderophores, and the like from the neuston, which is a critical environment in pelagic ocean biology.

Similar problems are found with organic materials as a genus, such as the rice crispies and peanut hulls proposed as float materials. While the use of "glass bubbles" as a float material is attractive, current supplies of hollow glass microspheres, as the term "bubble" would be understood by one skilled in the arts, are expensive and the Markels disclosures teach an organic binder or matrix selected from plastic, wax and starch wherein the glass bubbles are added to the matrix solely for buoyancy.

The work to date has also been criticized by others because supplementation with the limiting nutrient in one area will necessarily deplete the water body of other nutrients, which then become limiting as the water body moves out of the test area. In other words, while some hope to profit by fertilizing within a fence, the profit is robbed from areas outside the fence, a classical retelling of the tragedy of the commons. As an example, see U.S. Pat. No. 6,729,063, where the problem is made transparent. The method of first measuring limiting nutrient concentrations in a body of water and then supplementing that body of water with an excess of the most needed nutrient or nutrients is thus fundamentally flawed, and increases productivity in the test site by robbing the productivity of adjoining areas. To the extent that this is also the Martin Iron Hypothesis, the hypothesis has been highly instructive and successful, but is flawed as a method for rational geoengineering.

In short, the prior art has taught inter alia that higher bioavailability of the nutrient supplement is preferable, that formation of insoluble hydroxides of metals is unfavorable and is prevented by chelation, and that pulse administration is necessary to prevent eutrophic blooms. But what if there was a better way?

There remains a need for a composition of a marine fertilizer formulated to overcome the above disadvantages and to provide for sustained release of a balanced palette of micronutrients over a growing season or more. Such a composition may be of benefit in increasing harvestable species while also sequestering atmospheric carbon dioxide. Valuable characteristics of such a composition include provision of increased surface area for habitat, providing spatial richness of niches as well as a nutritive leachate (noting that surface chemistry and biochemistry is sufficient, i.e. not requiring exogenous chelators, to ensure that bioactive mineral forms are released at equilibrium rates for uptake). Changes in redox species of a mineral are achieved simply by supplying a surface on which they may be bound, eliminating the need for what is meant in the chemical art by "chelators". Because surfaces alone also result in "passive" shifts in the equilibrium concentrations of the redox species toward slow sustained release of soluble species and further supply habitat niches for microbiota that further modify the release of those mineral species as native organic complexes, accumulation of biomass is highly favored. This biomass can result in macro-sedimentation or can be harvested, or a combination of both, and is net new production. In preferred forms, these compositions are buoyant to ensure a $T_{0.5}$ of greater than 3-6 months in the photic zone and are optionally reflective on a skyward surface so as to provide immediate SST cooling. Light is not limiting except seasonally at polar latitudes!

An area of particular interest involves the design of nutrient formulations to promote the growth of particular community foodchains and the associated primary producers. For $CO_2$ sequestration, for example, it may be preferable to select a formulation that promotes the growth of coccolithophorids in preference to diatoms. *Phaeocystis antarctica* takes up twice as much $CO_2$ per mole of $PO_4$ removed than do diatoms, it has been reported. Foraminifera deposit calcium carbonate shells, a preferred sequestration and deposition mineral. Optionally, for cloud formation (termed here "kumogenesis"), it may be useful to increase dimethylsulfide production by selection of an enrichment medium that increases expression of the prymnesiophyte-microzooplankton envirotype (see Boyd P W et al. 2000. A mesoscale phytoplankton bloom in the polar southern ocean stimulated by iron fertilization. Nature 407:695-702). At some surface fill factors, gas exchange is reduced, but this can be adjusted or even overcome by physical design of the formulation. Referring again to the CLAW hypothesis formulated by Charlson, Lovelok, Andreae and Warren (Nature 326:655-661, 1987): dimethylsulfide (DMS) is thought to play a role in regulating the temperature of the planet by regulation of kumogenesis and associated cloud albedo. Dimethylsulfonio-propionate (DMSP) is biologically converted to DMS (a volatile compound), the main source of organic sulfur in the atmosphere above the oceans. Phytoplankton produce DMS that escapes into the atmosphere where it is oxidized to sulfuric acid, which acts as a nucleus for the condensation of water, and ultimately contributes to the albedo of the planet. According to the hypothesis, when cloud albedo increases, less solar radiation reaches the microbial plankton populations resulting in less photosynthesis and less DMS production, thereby creating a feedback loop that modulates the Earth's temperature [not allowing for the limiting effects of nutrients other than sulfur, which must complicate the model]. Experiments have shown that if the mixed layer depth is very shallow, then almost 100% of DMSP is converted into DMS, and as the mixed layer depth increases this value goes down. Using the mixed layer depth, chlorophyll concentrations and the DMS relationship, predicted DMS concentrations were nicely correlated with the real DMS concentrations in work by Rafel Simó and colleagues reported in Nature in 1999.

Provision of habitat in the form of bioactive surface area also has the effect of increasing trophic levels in rough proportion to the area and niche size of the habitat, a scalar porosity factor with a fractal dimension.

In contrast, current solution fertilization methods result in increases in dissolved organic carbon, picoplankton and, if sustained, bloom populations of micro-grazers such as copepods with associated anoxia and collapse of active photosynthesis. Any increases in $CO_2$ uptake are transitory.

In the oligotropic ocean, picoplankton predominate. The fecal sediment fall is thus a "micro-sediment" with poor sedimentation characteristics that is rapidly re-solubilized as $CO_2$ and organic acids by the action of heterotrophs. Regeneration of $CO_2$ continues into the mesopelagic zone due to the slow descent and long residence time of the microparticles. It is well established that pelagic "microzooplankton" are the principal grazers on marine phytoplankton (Billett, D et al. 1983. Seasonal sedimentation of phytoplankton to the deep-sea benthos. Nature 302:520-522; Ryther, J H. 1969. Photosynthesis and fish production in the sea. Science 166:72-76; Falkowski, P G et al. 2000. The global carbon cycle: a test of our knowledge of the Earth as a system. Science 290:291-294; Turner, J T et al. 2000. Accumulation of red tide toxins in larger size fractions of zooplankton assemblages from Massachusetts Bay, USA. Mar Ecol Prog Ser, 203:95-107; Smayda, T J. 1970. The suspension and sinking of phytoplankton in the sea. Oceanogr Mar Biol Ann Rev 8:353-414; Irwin A J et al. 2006. Scaling-up from nutrient physiology to the size-structure of phytoplankton communities. J Plankton Res 28:459-471; Richardson, T. and Jackson, G. 2007. Small phytoplankton and carbon export from the surface ocean. Science, 315:838; Zarauz L et al. 2009. Changes in plankton size structure and composition, during the generation of a phytoplankton bloom, in the central Cantabrian sea. J Plankton Res 31:193-207). Micro-sediment sinks more slowly and is more likely to be re-solubilized. The result is that relatively little micro-sediment crosses the "100-Year Horizon" at depth as required for permanent sequestration and a significant fraction of inorganic carbon accumulates in the mesopelagic zone.

As disclosed here, this can be seen principally as an effect of habitat size, and the primary geoengineering intervention that can increase the size and quantity of sediment is not nutrient level but is instead habitat size and complexity, which effectively correlates with size of organism, number of trophic levels, and size and speed of sedimentary deadfall due to larger particle size. With provision for habitat and nutrient levels capable of supporting higher trophic levels as taught here, "macro-sediment" is obtained, and there are associated significant increases in $CO_2$-derived organic matter descending below the 100-Year Horizon. Not only is net productivity increased, but the quality of the deep ocean fixed carbon efflux (or "biological pump") is improved.

Ocean productivity in the form of net biological carbon assimilation is variously estimated at 36-48 GtC/yr, globally in aggregate, an impressive number. This marine productivity is about half of all global productivity, but is spread over an area of about $361 \times 10^6$ $km^2$ (almost three times the area of terrestrial ecosystems). Blooms can yield 50 $gm/m^2/day$ of new fixed carbon but it is more typical to encounter oceans where productivity is on the order of 3-5 $gm/m^2/yr$. Corridors of higher productivity tend to be localized, geographically limited, and seasonal (such as coastal upwelling or at the equator) and a method for increasing productivity in less productive areas of the ocean has been long sought. As discussed above, nutrient limitation is the primary throttle on marine productivity over much of this "ocean desert" and habitat is the key to increasing sediment size. The effect can be dramatic, while current sequestration flux to the benthos in the form of "marine snow" and fecal pellets may be on the order of 0.43 GtC/yr out of global marine productivity of 50 GtC/yr (with an open ocean component of 10 GtC/yr), less than 10% of pelagic sediment actually reaches the ocean floor. Sinking rates for coccoliths in pellet form are 160 m/day versus 0.15 m/day for the discrete coccoliths; and fecal pellets sink at rates up to 2000 m/day [Huneke H and R Henrich. 2011. Pelagic sedimentation in modern and ancient oceans. In, Deep-Sea Sediments. Huneke and Mulder (eds) Dev Sedimentology 63, page 222-231]. Thus, although current open ocean output as a sink for fixed carbon of 0.4 GtC/yr compares poorly to an annualized human carbon output equivalent to 6-7 GtC/yr, any endeavor that increased surface steady state sediment production from 0.001 $gm/m^2/day$ to 1 or 3 $gm/m^2/day$ (a $10^3$-fold increase) in a form that sediments rapidly is expected to have a dramatic planetary cooling effect in a short period of time if deployed over sufficient surface area. Biological communities such as eelgrass and coral reefs having stable productivity of 1-3 $gm/m^2/day$ are readily identified. On the scale of industrial production, devices of the invention covering 150,000 $km^2$ or 300,000 $km^2$ (somewhere around the size of Wyoming) may be contemplated at a cost that is substantially less than the alternatives.

The compositions and methods of the present invention bring welcome synergy to convergent interests: global warming, marine productivity, and carbon sequestration. A combination of modalities—modification of global albedo and enhancements in marine productivity with associated increases in sedimentary lithification of atmospheric $CO_2$—addresses the global climate crisis in multiple ways. There is a need for geoengineering that overcomes the dangers and difficulties discussed in the introductory remarks here, at a scale likely to have a significant impact on the global energy balance, while further providing some added economic benefit in the form of commodities or carbon credits so as to have a measurable incentive for implementation. Needed is a solution with a near-instantaneous effect that is readily measurable in direct physical terms, is rapidly deployable, and yet can be allowed to dissipate or vanish of a timescale of one or more years following implementation, without further intervention. In short, as will be shown here, reflective forced cooling of the planet is a plausible answer to the problem of global warming and can be fitted into a business model with appropriate incentives. Similarly, geoengineering of the atmosphere by marine sequestration of carbon dioxide at depth is also doable and can be incentivized for investment. Devices, methods and means for achieving these ends are aspects of the invention as laid open herein.

SUMMARY OF THE DISCLOSURE

It is clear that prior art efforts at fertilization of the sea have focused on high bioavailability—unnecessarily. A healthy neuston provides an excess of chelators, why add EDTA? The prior art teaches against application of elemental iron because iron forms hydroxides that rapidly precipitate out of the photic zone. But must elemental iron necessarily precipitate from the photic zone? These tenants of the prior art, and others, are challenged here.

Prior art efforts have sought to drive marine productivity by increasing the concentration of select essential elements, primarily iron, but have taken no notice of the effect of solid:water interface on partition coefficients, solubility constants, and biological activity. Merely increasing surface area in the ocean, absent any other effort, is sufficient to stimulate accumulation of biomass. The right combination of new surface area and increased nutrient supply, over an extended period of time, will result in superior performance of any biological system. More complex ecosystems are more stable and more productive over time. Complexity is both richness in trophic levels and in spatial niches, the fractal dimensions of Nature.

Described here in a first embodiment are compositions, apparatus, and methods for biological and physical geoengineering. Disclosed are buoyant inorganic particles, prill, pucks, or floats having several properties: 1) a sustained-release composition for delivery of nutrients and minerals selected from iron, calcium, magnesium, zinc, copper, manganese, molybdenum, cobalt, chromium, nickel, vanadium, silicon, boron, cadmium, selenium, sulfur, inorganic nitrogen, and phosphate, resulting in increased biological productivity (ie. food), while synergically, 2) the compositions increase surface area for biochemical and photosynthetic activity in the neuston (ie. uptake of carbon dioxide), and 3) the compositions comprise a light-reflective skyward surface for increasing albedo when applied to bodies of water and are buoyant. These compositions are found to A) increase the potential for pelagic aquaculture, B) increase validated carbon sequestration and lithification, and C) provide some immediate relief from global warming by directly increasing planetary reflection and indirectly by increasing cloud nucleation activity. An installation in one location can influence albedo downwind in other segments of the atmosphere by kumogenesis. Preferred compositions are buoyant, essentially inorganic, and light reflective. A preferred composition comprises a mixture of inorganic salts and binders (such as an inorganic glass) effective for increasing the growth of primary aquatic ecosystems such as coccolithophorids, diatoms, silicoflagellates, dinoflagellates, and microalgae (so-called "picoplankton") in a sustained-release composition having a $T_{0.5}$ of 0.5-3 years. Validation apparatus for assessing $CO_2$ sequestration are illustrated, and include vertical spar buoys designed to resist wave action while providing a stable long-term platform for "big science" oceanography—supporting at depths an instrument package with field of laser particle counters for measuring the $CO_2$ biological pump effect of sediment fall past the 100-Year Horizon, while not limited thereto.

These considerations have been unappreciated. In the dire situation in which we find ourselves, the goal must be not short term profit, but the long term productivity of the ocean at sustainable levels, with a significant part of that productivity diverted to carbon sequestration at the ocean bottom and in deep sea currents having circulation times measured in centuries. Therefore, it is appropriate to design and optimize sustained release compositions the half-life of which is measured in months or years, not days or even weeks. Such matrices are necessarily "stone-like" in nature—inorganic—and buoyant in water, an unlikely natural combination. But not impossible. There is added benefit by forming matrices having complex fractal surface topology at microscopic and macroscopic scales. In a preferred embodiment, the skyward facets of these compositions are reflective, thereby instantly modulating the albedo of the body of water upon which they are deployed. In other preferred embodiments, the matrices form habitat to support primary producers and complex food-chains, resulting in macro-sediment that rapidly falls to the ocean floor.

The geoengineering devices and processes disclosed here combine biological and physical means for reducing global warming, increasing oceanic productivity, and are readily deployed on ocean surfaces. In one aspect, the invention is an inorganic, buoyant material for sustained release of a balanced mineral fertilizer. The fertilizer is balanced with trace and macro minerals and nutrients to support photoautotrophic growth where $CO_2$ is the principle source of carbon. By sustained release, a half-life $T_{0.5}$ of 0.5 to 3 years is contemplated. Mineraline compositions of the invention include compositions of iron, calcium, magnesium, and zinc with trace amounts of copper, molybdate, manganese, cobalt, chromium, borate, selenium, vanadium, and nickel, optionally supplemented with inorganic nitrogen such as nitrate, with phosphate, with sulfur or sulfates, and with blowgas enriched in $CO_2$, or other source of carbonates. Siliceous material is also a useful supplement for some target populations. The compositions take the form of a prill, a puck, a pontoon, or a buoy, forms referred here generically as "sustained release compositions" (SRC).

In another embodiment, the invention is a method for conveying nutrient-rich water from below the photic zone to the ocean surface using renewable energy for pumping. Advantageously, deep water is well balanced in nutrient composition to support active photosynthesis. In a typical transect with depth, the profile of iron concentration will vary from 0.03 nM Fe at the surface to 0.1 nM at 100 m, to 80 nM at 250 m, and to 125 nM at 500 m, where a plateau is reached. Thus significant benefit is obtained by pumping water from below 100 m to the surface. Because water rises in a pipe to seek its own level, pumping resistance is not a factor of head height so much as it is resistance to pipe flow. Relatively low energy input is needed.

In another aspect, the invention is a buoy or buoy array for scientific investigation of the effects of the above compositions on albedo and on carbon sequestration in an aquatic environment. The buoy floats with an extended vertical axis for stability independent of wave height and supports a surface platform for instrumentation and pumps for controlling depth. The buoy may be associated with one or more rigid or semi-rigid rings which serve as restraints to disperse floating habitat. In another aspect, the buoy is a platform for aquaculture. Elements of the platform are equipped with active and passive buoyancy means and are submersible in the event of major storms or swells.

In another aspect, the invention is an apparatus for emitting a unit quantity of solar exsolation measurable in Joules from a terrestrial reflective surface to a plane above the upper terminus of the troposphere, wherein a solar exsolation credit instrument equal to the unit quantity of solar exsolation is produced and validated by the apparatus. Solar exsolation credits produced are optionally traded in a market or otherwise dispensed as credits against energy consumption, heat outputs associated with energy consumption, or greenhouse gas emission. A market for trading a solar exsolation credit will generally comprise a means for tracking and displaying an ask price and a bid price, and a means for executing trades such as are known in commodities markets. Other aspects of the invention will be apparent as discussed below.

In yet another aspect, the invention is a continuous method for extracting carbon dioxide from the air and exporting it as fixed carbon to the oceanic abyss below the 100 year horizon. A means for creating a credible market for trading validated carbon credits is demonstrated.

Global Scale Feasibility Calculations

1. Albedo

It has been shown experimentally that increases in albedo can force large scale local cooling. In a recent publication, Campra (2008, J Geophys Res 113:1-10) reported a long term study of 26,000 hectares in southern Spain, where installation of greenhouses, in what is described as "a continuous greenhouse-covered surface," has resulted in a positive increase in albedo of about 0.1. This increased albedo was associated with reflective heat transfer averaging −20 W/m$^2$ (i.e., cooling) by MODIS satellite infrarometry. Aerial photos confirm that the surface is extensively whitened by whitewashing the glass roofs of the structures. Terrestrial solar radiation IN is about 340 W/m$^2$; therefore a reflective component of 20 W/m$^2$ OUT is highly significant if integrated over a large enough surface area.

In short, surface albedo can be used to reverse global warming. A plume of floating pelagic reflective pucks, dispersed across the equatorial oceans over an area of $2.2 \times 10^6$ km$^2$, a surface area the size of Greenland, and resulting in a change in albedo of +0.1, will result in perceptible global cooling in a matter of days or weeks, as can be verified by MODIS satellite infrarometry. Taking global surface insolation at 45 PW, the net effect of 20 W/m$^2$ forced cooling by reflection to space over this surface area (44 GW) is an essentially instantaneous −0.1% change in the global surface net energy balance.

Interestingly, assuming a total urban landscape of about $2.2 \times 10^6$ km$^2$ and an increase in albedo of just 10% (as by whitewashing all roofs and roads or by installing white vinyl roofing and high albedo pavement), a similar degree of cooling will be achieved. Thus an apparatus for achieving solar exsolation will include a reflective surface and a means for validating the amount of solar exsolation. The dispersable reflective compositions disclosed here have multiplier effects: increasing albedo, increasing marine productivity, and increasing sedimentary deadfall.

2. Marine Sedimentary Sequestration

Enhancement of annualized pelagic sedimentary deadfall in an oligotropic ocean site selected for research is expected to increase from 0.0001 gm/m$^2$/day (reaching the seafloor) to 3 gm/m$^2$/day. Assuming an installation of 360,000 km$^2$, sequestered carbon increases from 0.00001 GtC/m$^2$/yr to 0.4 GtC/m$^2$/yr as fixed carbon sedimented below the 100 Yr horizon. Higher efficiency of sedimentation results from increased sediment size. Combining the sedimentation of the test patch with an annualized 0.4 GtC/m$^2$/yr for the rest of the ocean, the total is more than 10% of human $CO_2$ release by fossil fuel consumption (currently almost 7 GtC annually), a significant amount. Not included are cooling effects related to cloud formation and increased reflectivity. Synergic effects are noted and increased marine productivity results in harvestable biomass. Carbon sequestrations are sold in proportion to the validated increase in sedimentary deadfall below the 100 Yr horizon.

BRIEF DESCRIPTION OF THE FIGURES

The teachings of the present invention can be readily understood by considering the following detailed description in conjunction with the accompanying drawings, in which:

FIG. 15A is a half-section or outline view of a hollow, columnar buoy for marine field work on carbon sequestration and ocean albedo. FIG. 15B provides dimensions of a buoy designed to float with a waterline as shown. FIGS. 15C, 15D and 15E depict a transverse and axial sectional view of the buoy shaft. FIG. 15F plots buoyant volume (displacement in $m^3$) versus depth or draft on the structure shown.

FIG. 21 is an integrated view of a free-floating research station, with floating pontoon booms as part of an aquaculture/marine fertilization facility and with a spaceframe and instrument package suspended by cables below the 100 Yr-horizon for validating carbon sequestration by measuring sediment fall along a transect or over a sampling area.

FIG. 22 describes steps for initiating validated $CO_2$ remediation using the apparatus of the invention.

FIG. 26 diagrammatically outlines steps in a method to continuously supply nutrients to the upper water layers and neuston so as to increase biomass and net carbon sequestration.

DETAILED DESCRIPTION

Figure 1:
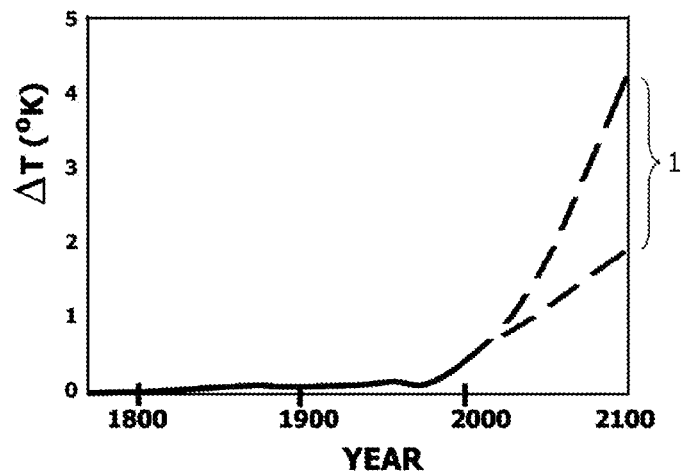
FIG. 1 is an extrapolation from best available models of global warming. The current range (1) of best estimates (IPCC: Climate Change 2007) for mean global temperature increase by 2100 is 1.8 to 4.0° C. The next report from the IPCC is due in 2014.

Although the following detailed description contains specific details for the purposes of explication, one of skill in the art will appreciate that many variations and alterations to the following details are within the scope of the invention. Accordingly, the exemplary embodiments of the invention described below are set forth without any loss of generality to, and without imposing limitations upon, the claimed invention.

Albedo—is the fraction or percent of reflected light from a surface as a ratio over the total incident illumination. Global albedo is the fraction of incident solar energy reflected from the Earth back into space. Albedo, in other words, is the ratio of exsolation to insolation, where exsolation is the quantity of reflected light exiting the atmosphere. A total energy balance for the planet reduces essentially to the energy of photonic insolation minus the sum of photonic and phononic out-radiation. As a matter of experimental convenience, meaningful insights into albedo can be made by comparing incident light and reflected light off a terrestrial surface. Since this incident light is largely depleted of wavelengths interacting with atmospheric species, visible reflected light is a significant component of global albedo. Several values for albedo are listed in the following table.

|  | Albedo |
| --- | --- |
| Snow and ice | 0.30-0.85 |
| Clouds | 0.35-0.75 |
| Desert | 0.25-0.30 |
| Forest | 0.05-0.15 |
| Open water | 0.05-0.08 |

Coefficient of reflection—the ratio of the total amount of radiation, typically visible light, reflected by a surface to the total amount of radiation incident on the surface. Preferably, reflective surfaces generally have a reflectance coefficient greater than 0.5. Some reflective surfaces are mirror-like. The reflective coefficient is measured by shining white light on a surface and measuring the ratio of reflected light to incident light.

Biocompatible—of a form that may be contacted with a food-chain in an aqueous environment without harm to number or diversity of trophic levels.

Net aggregate positive buoyancy—denotes a composition which displaces a volume of water having a weight greater than the weight of the composition. The composition typically contains a gas-filled void volume enclosed or dispersed in an inorganic matrix.

Mineraline—an inorganic form of an element selected from elemental, salt, oxide, hydride or hydrate, and generally confined to Groups I through VI of the periodic table, exempting lanthanides and actinides, and for the present purposes, typically limited to biocompatible elements selected from rows 2 through 6. Mineraline compositions are generally free of organic compositions. Mineraline compositions of the invention include compositions of iron, calcium, magnesium, and zinc with trace amounts of copper, molybdate, manganese, cobalt, borate, chromium, selenium, vanadium, and nickel, optionally supplemented with nitrate, phosphate, and with blowgas enriched in $CO_2$, or other source of carbonates. Siliceous material is also a useful supplement for some target populations and is a suitable inorganic binder.

Phosphorus supplementation is also contemplated, generally in the form of mineraline phosphates. Because the elemental composition of phytoplankton is generally C:N:P=106:16:1 (commonly referred to as the "Redfield Ratio"), about 100 units of carbon are delivered to the deep sea for every unit of phosphorus assimilated by phytoplankton in the photolayer and sedimented into the abysmal plains and trenches. This is the "biological pump" that delivers carbon from the atmosphere to the deep sea, where it is concentrated and sequestered for centuries.

100-Year Horizon—is a somewhat arbitrary functional boundary separating marine sediment-associated carbon that is recycled as part of the active food chain (and hence re-emerges as $CO_2$ by respiration) and carbon associated with sediments that are sequestered from the atmosphere for geological periods of time or ultimately remineralized. The 100-yr horizon has been proposed as a benchmark for validating carbon sequestration credits.

SRC—refers to "sustained release composition", that is, inorganic mineraline formulations in the form of a granule, pellet, puck, prill, microsphere, pontoon, sheet, plate, or agglomerate having a positive buoyancy. The compositions release physiologically acceptable concentrations and forms of elements required for photosynthesis with sustained release kinetics. The shell, the core, or the matrix of the solid member typically contains a gas phase. SRC with porosity or a fractal roughness are also provided. A buoyant core may be coated with a sustained release layer. Optionally, these formulations are light-reflective or are prepared with a reflective surface. In a preferred composition, the formulation floats with a reflective surface oriented skyward.

Cenospheres, vermiculite (exploded mica) and composites of vermiculite or perlite and kaolin, talc, pumice, exploded clays, zeolites generally, scoria, $CaCO_3$, or glass, as well as artificial foamed silicates made from hydrosols are other potential inorganic substrates for SRCs. One type of cementitious, spray-foam insulation is known as Air-Krete™. It contains magnesium silicate, has an initial consistency similar to shaving cream, and is fireproof. For many years, hollow glass microspheres have been available in quantity and may be used to impart buoyancy to inorganic formulations made with an inorganic binder. Unlike ordinary glass microspheres, retro-reflective glass microspheres are well known for their use in bright reflective surfaces. Such microspheres have refractive indexes in the range of 1 to 3 and are suitable reflectors even when immersed in water. Glass microspheres may be coated with a variety of metallic reflectors. Ceramic and metal hollow microspheres are also commercially available. Manufacture of hollow microspheres is readily accomplished, taking advantage of the interfacial tension of a gas in glass collet, and a process equivalent to Ostwald ripening at temperatures at which the substrate is plastic. Formulations made of foamed clays are also provided.

Float—refers to a pontoon, raft, barge, boom or other displacing structure that is larger than a prill or a puck. Also comprises pontoon structures and combinations thereof. Floats may be individually dispersed or tethered.

Trophic levels—refers to one or more pools of carbon in a food chain. Typically a "primary producer level" or levels occupies the base of the food chain. Direct grazers occupy a second level. Larger predators occupy a third level, and so forth. Over the past 25 years our vision of the pelagic food web structure has changed dramatically. We now view the traditional "diatom-copepod-fish" foodweb as a relatively minor component. The food web consistently present in all oceanic habitats is based on pico- and nanoplankton-sized autotrophs and heterotrophs, which are efficiently grazed by flagellates and ciliates. The pelagic food web is microbe-centric. ("Microbe" in this context means small autotrophs, heterotrophs, and mixotrophs, and refers to both prokaryotes and eukaryotes.) A necessary effort in carbon sequestration is an effort to shift the food web to include higher trophic levels. The principal means for doing this is by supplying habitat and solid phase surface area, not merely iron.

Turning now to the figures, FIG. 1 is a representation of future global temperatures given current trendlines. Shown are high and low "best estimates" prepared by the IPCC. The difference 1 between the two dotted lines represents the current uncertainty.

Figure 2:
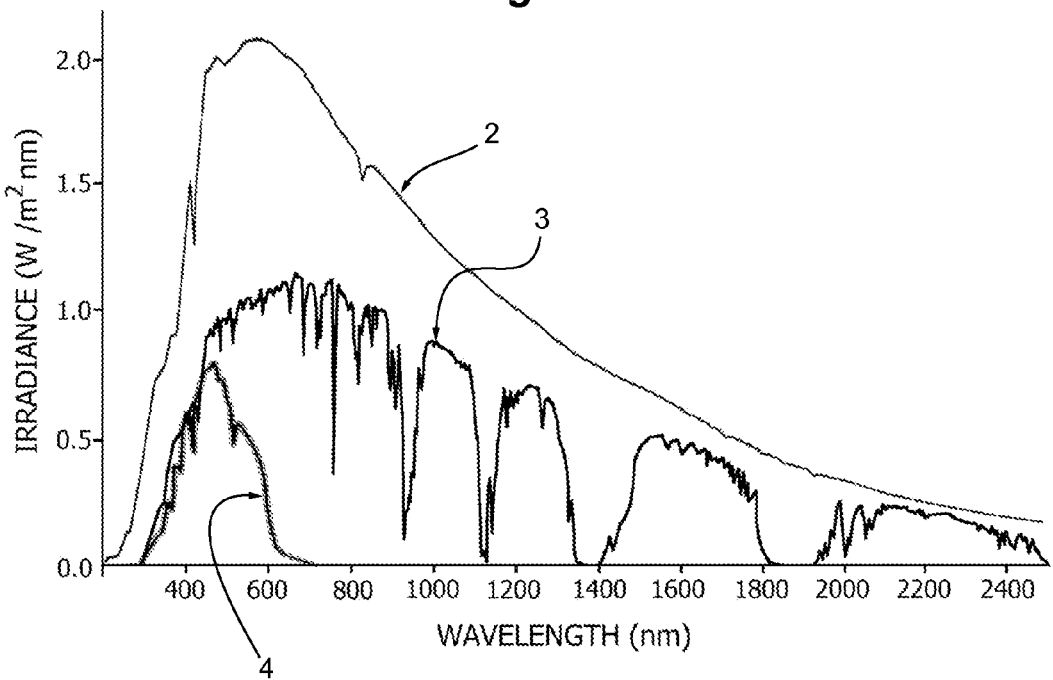
FIG. 2 is an adaptation of a spectrogram of solar radiation as received at the top of the atmosphere (2), at the surface at sea level (3), and at a depth of 10 meters below an ocean surface (4), for wavelengths from the UV to the far infrared.

FIG. 2 shows a spectrogram of incident solar irradiation as a function of wavelength and altitude, the upper curve showing solar energy ($W/m^2$-nm) entering the atmosphere (2), the middle curve light energy striking the surface of the ocean (3), and the bottommost curve (4) light having been depleted after penetration to a depth of 10 m below the ocean surface. The area under curve 3 and above curve 4 is the light energy converted to heat in the top 10 m of ocean. Clearly all light entering a deep body of water is fully absorbed. The oceans, covering more than half the surface of the globe, are thus major engines of climate. Reducing this heat engine is a rapid and effective way to force global cooling.

Figure 3:
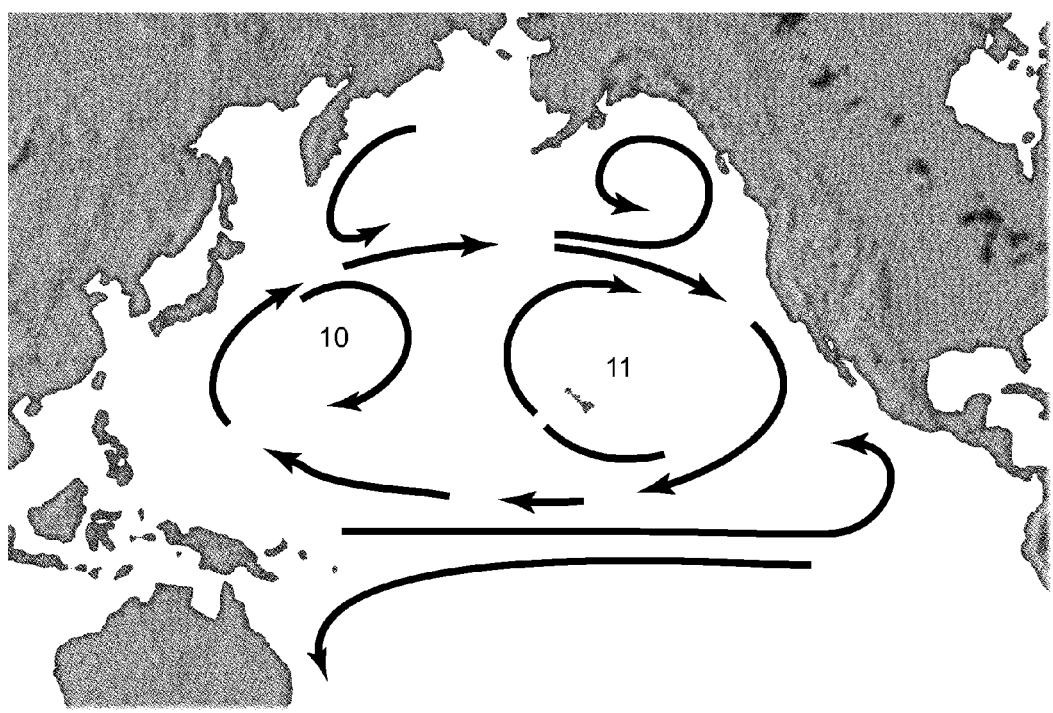
FIG. 3 is a map of the Pacific ocean showing approximate locations of the Pacific NW and NE gyers.

FIG. 3 is a map of the Pacific ocean showing the approximate locations 10, 11 of the NW and NE gyres, and general patterns of circulation of currents. The gyres are known to accumulate plastic detritus at their centers.

Figure 4:
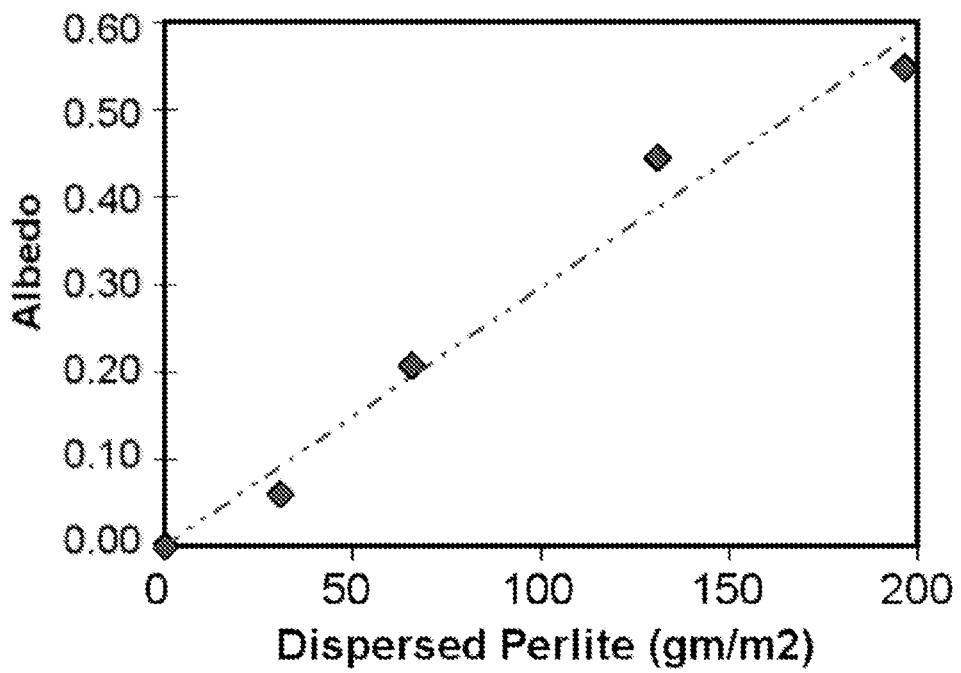
FIG. 4 is an experimental result, shown relative density of perlite as reflector on water and the corresponding albedo measured with a solar collector and using incident radiation as a denominator.
Figure 5:
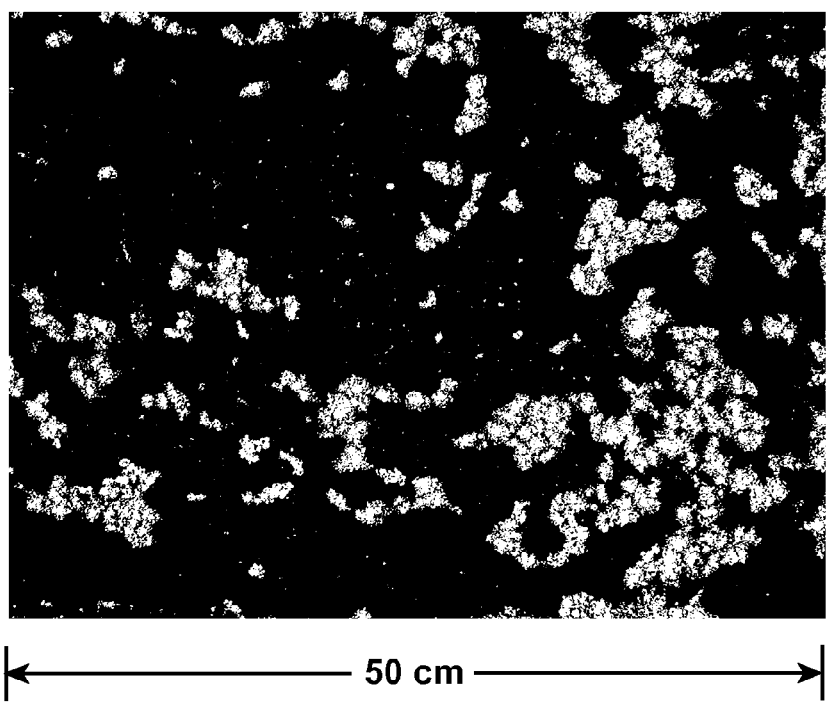
FIG. 5 is a view of a water-filled experimental tank containing 30 gm/m$^2$ perlite dispersed at a partial fill factor on the surface of the water.

FIG. 4 is a plot of data from an experiment in which prill (perlite, horticultural grade) is weighted out and dispersed on a defined surface area in a dark-bottomed tank filled with water. This material contains a significant proportion of fines that contribute poorly to reflectivity. Perlite is a snow white material manufactured by "exploding" a porous, moist mineral found in deposits associated with volcanic ash and pumice. For the experiment, incident radiation was measured amperometrically with a solar panel and conditions were selected where the current response was generally linear. The effect of increasing quantity of reflective prill was then tested by turning the solar panel upside down over the tank (with incident light at about a 30 degree angle) and measuring the reflected light in the same way. A zero-intercept was obtained experimentally when no prill was added to the tank. A fill factor can be estimated from photographs taken during the experiment (such as FIG. 5). Even at 30 $gm/m^2$, increases in albedo of the order of +0.05 were obtained. This is a highly significant change in energy flux if taken over a very large surface area. FIG. 5 is a b/w reproduction of a photograph of an experimental setup as described above, although the sun was slightly higher in the sky. A fill factor of 30 $gm/m^2$ perlite is shown. Some clumping of the perlite is observed.

Albedo at high fill factors of floating perlite on water approaches 0.6. By comparison, the albedo of snow is typically reported as 0.3-0.85, depending on the cleanness of the snow.

Figure 6:
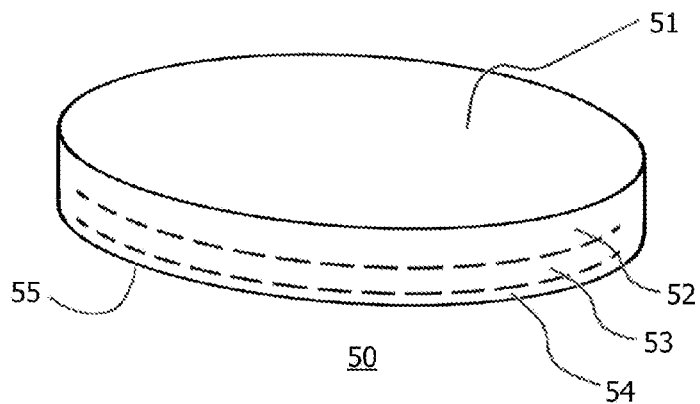
FIG. 6 is a sketch of a composite SRC in the form of a puck.

FIG. 6 is a schematic view of a puck (50) formed with multiple layers. The upper surface (51) is a reflective surface and for example is comprised of titanium oxide, silicon oxide, zirconium oxide, or glass, and may contain platelets of mica or metal or crystals of olivine, or other reflective material such as a thin mirror layer of aluminum. The upper layer (52) is rich in low density materials for positive buoyancy and is optionally comprised of perlite in an inorganic binder of waterglass or exploded porcelain, for example. The middle layer (53) includes a slow release matrix and contains mineraline inorganic nutrients selected from iron, calcium, magnesium, zinc, copper, molybdate, manganese, cobalt, borate, selenium, vanadium, and nickel, optionally supplemented with nitrate and phosphate. The minerals are supplied as oxides, nitrates, carbonates, silicates, sulfates, or as elements. The redox state of the minerals is selected for cost and convenience in formulation because bioavailable redox species are formed in situ. The matrix is formulated so that the elements are released in biologically nutritive quantities over an extended period of time, preferably the matrix dissolves with a half-life of 0.5 to 3 years. This middle layer is formulated with a higher density, as ballast, so that the puck is likely to float with the upper layer facing skyward. A lower layer (54) may be added for quick release, and also serves to reduce fouling by virtue of its higher erodibility. The net buoyancy of the puck is positive. A porous coat (55) such as a leachable glass may also be added to improve handling during transport and dispersal.

Various methods known in the art may used to make porous sustained release materials from ceramics. The polymeric-sponge method produces open-cell structures by impregnating a polymeric sponge with a ceramic powder slurry, the organics are then driven off at a temperature below that required for firing the ceramic slurry material. Polymers sponges include polyurethane, cellulose, polyvinyl chloride, polystyrene, and latex. Alternatively, a direct foaming method can be used to produce both open-cell and closed-cell structures. In this method, a chemical mixture containing the desired ceramic component and gas precursors is treated to evolve a gas. Bubbles in the material cause it to foam. The resulting porous ceramic material is then dried and fired. Honeycomb structures may also be made. Firing the green ceramic typically involves a temperature of 1000-1700° C., however, improvements have been made that significantly reduce the firing temperature as described in U.S. Pat. No. 7,169,725 to Haun, and adaptations thereof. Porous ceramics can also be made by freeze drying a precursor followed by sintering (see for example: Deville, S. 2008. Freeze-casting of porous ceramics. Adv Engin Matls 10:155-169), and adaptations thereof. Sol gel and water glass methods may also be use.

Figure 7:
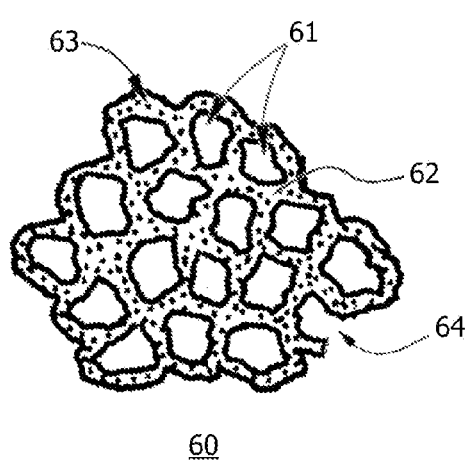
FIG. 7 is a section through a composite SRC granule or prill.

FIG. 7 is a cartoon showing a section through an amorphous SRC granule or prill (60). Voids (61) filled with gas are used to reduce the aggregate density, because the particle must float. A glass or ceramic matrix (62) material is used to bind mineraline elements (63) into a solid granule. Voids (64) on the surface of the particle increase surface area, promote surface chemistry, and facilitate colonization with microorganisms that will erode the matrix over multiple months or even years. The matrix material is a clay or a glass, for example a silica glass or kaolin, while not limited thereto. The granules (60) are preferably white or are optionally coated with embedded specular reflectors such as glass microspheres or quartz or mica platelets. The granules or pellets may contain a single void. Glass floats used in the early part of this century by Japanese fishermen have been known ride the Kuroshio current north, circling the Pacific for decades and in fact still wash up on Oregon and Hawaii beaches after storms. The spherical floats vary in size from a few centimeters to almost a meter in diameter, and even accumulate barnacles, eventually sinking under the accumulated weight.

Figure 8:
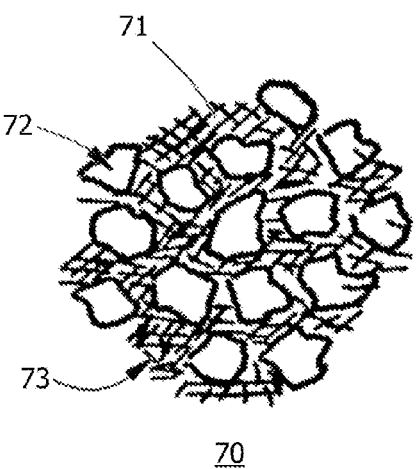
FIG. 8 is a section through a composite SRC granule with fibrous matrix.

FIG. 8 is a cartoon shown a section through an amorphous SRC pellet (70) with a fibrous low-density matrix (71). Granules (72) of a slow release material and fibers (73) are embedded in the matrix (73). Non-wetting voids in the matrix hold air sufficient for buoyancy. The matrix is typically a ceramic or a glass.

Figure 9A:
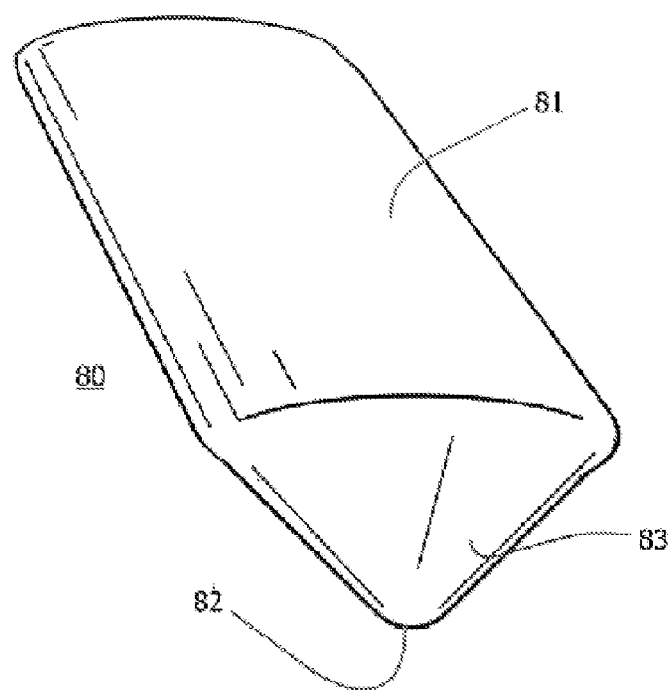
FIG. 9A is a perspective view of an extruded float and FIG. 9B is a cross-section of the float showing multiple layers.
Figure 9B:
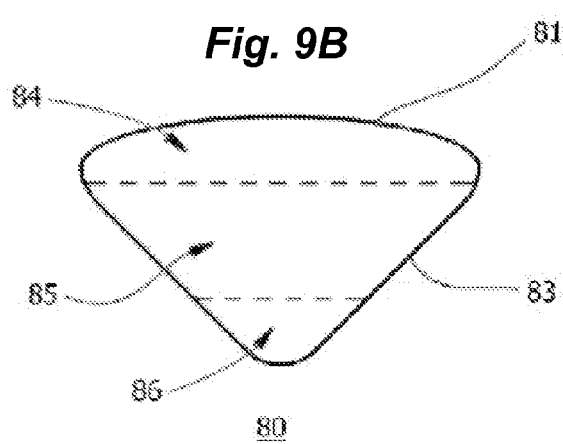

FIGS. 9A and 9B show an extruded product (80). This float is manufactured by cutting a ribbon of extruded matrix material into convenient lengths. Each float comprises a reflective cap (81), a ballasted keel (82), and a glass coating (83).

Figure 9C:
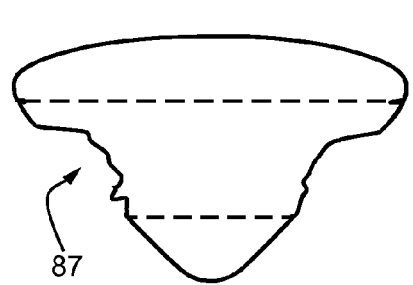
FIG. 9C shows erosion of an extended release layer of a float, increasing habitat surface.

FIG. 9B illustrates a section through a float of FIG. 9A. The float is comprised of three layers, an upper buoyant layer (84) with entrapped air, a middle layer (85) with mineraline elements formulated in a slow release matrix of neutral density, and a lower layer (86) with embedded iron filings and serving as a ballasted keel. The floats are spray coated with water glass or hard coat and sintered during manufacture. FIG. 9C is a sectional view through the float of FIG. 9A, showing the effect of biological erosion (87) characteristic of this sustained release composition.

Figure 10:
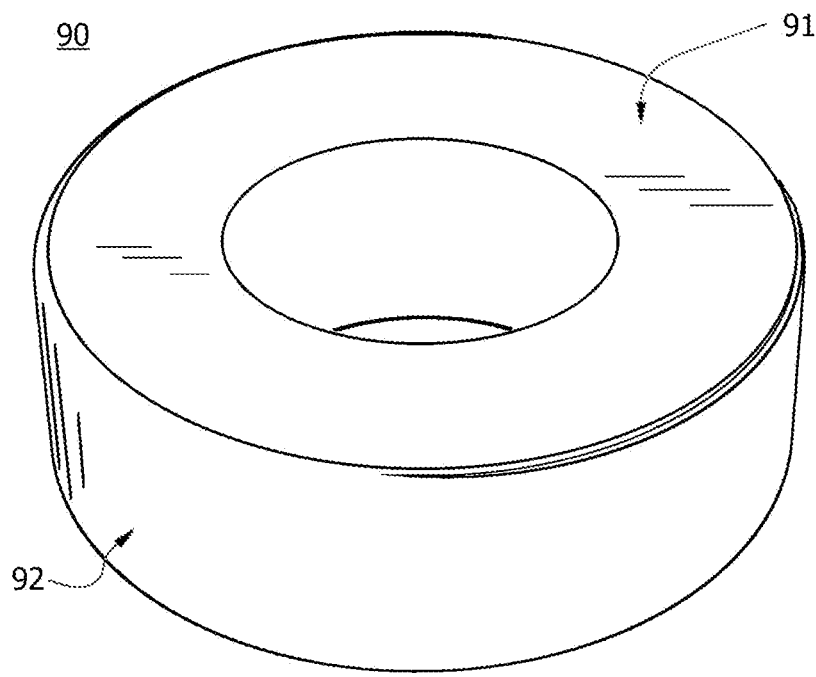
FIG. 10 is a sketch of a toroid puck with sustained release matrix and reflective cap.

FIG. 10 shows a toroid float (90) having a net positive buoyancy, a sustained release core, and a hard coat outer layer (92), the cap (91) with reflective properties. Floats may optionally be tethered together to form a net-like sheet when dispersed.

Figure 11:
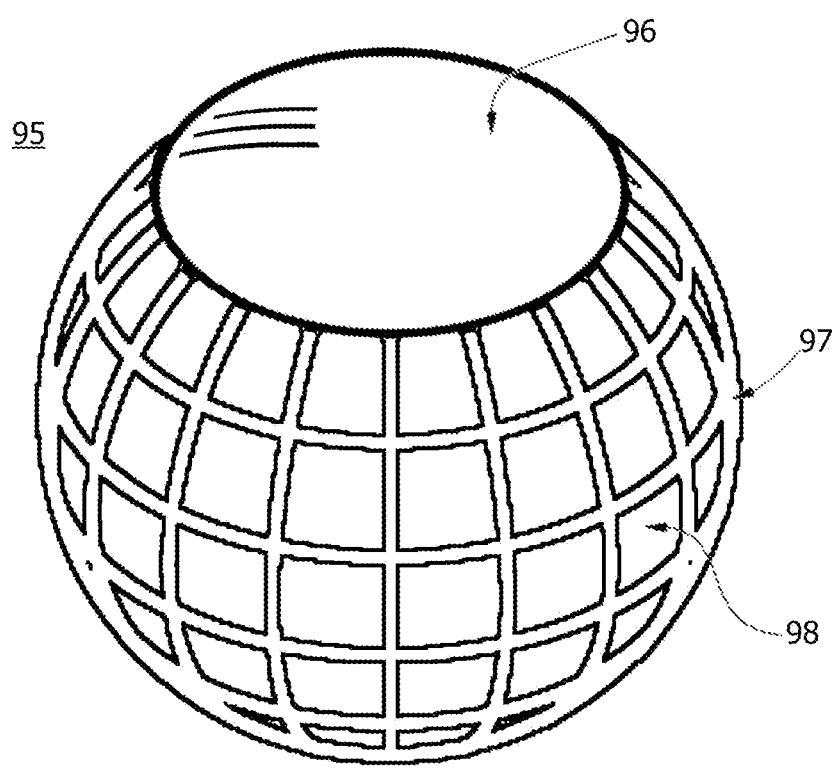
FIG. 11 is a sketch of a hollow ribbed spheroid float with buoyant cap.

FIG. 11 shows a hollow ribbed ball with a reflective cap (96) having a core of low density matrix material and erodible ribs (97) having a mineral composition for sustained release. The ribs are strengthened to resist breakage. Apertures (98) between the ribs permit the entry of organisms.

Figure 12A:
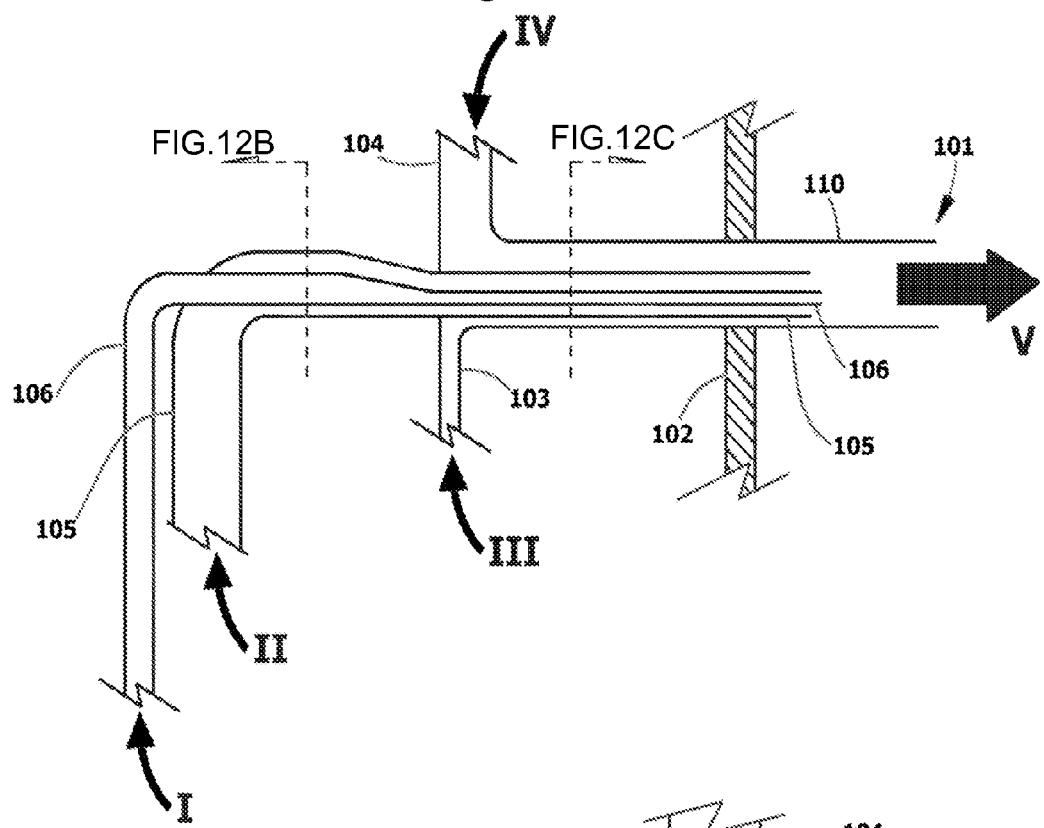
FIGS. 12A, 12B and 12C are schematics of an extruder for forming SRC floats in a continuous ribbon-flow process.
Figure 12B:
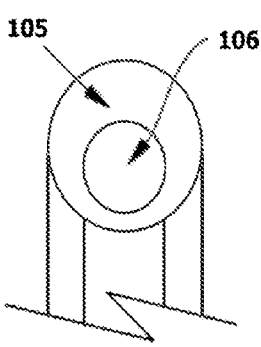
Figure 12C:
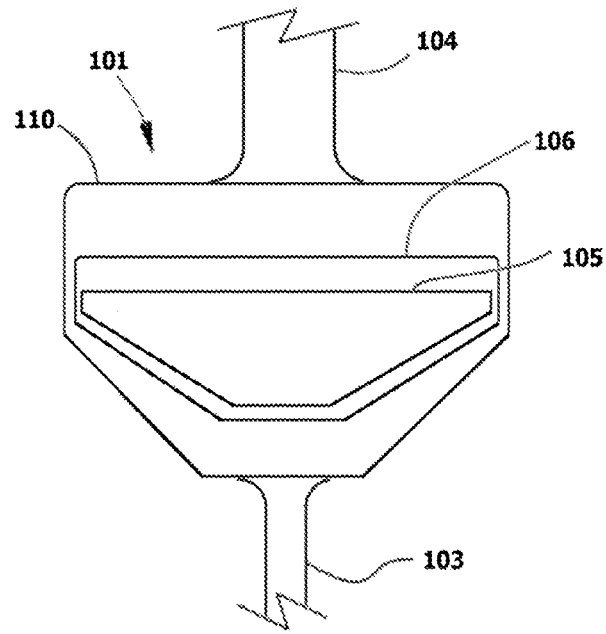

FIGS. 12A, B and C are illustrative of an extruder process nozzle used to manufacture the float of FIG. 9. Extruded product is indicated by V. Four feeds are fed into a triple nozzle (101) with outer sheath (110) that is inserted into an alcohol bath (111) through process tank wall (102). Feed III is the iron rich bottom layer in a clay matrix and is fed in at (103). Feed IV is a gas bubble rich upper layer of waterglass as a slurry rich in specular reflective material such as titanium oxide or mica platelets and is fed in at 104. Feed II is a core layer of slow-release mineraline elements important for photosynthesis in a waterglass slurry and enters through a nested tube (105). Feed I, entering the core of the extruded ribbon at 106, is an alcohol that solidifies the waterglass matrix and is removed and recovered during sintering under a $CO_2$ atmosphere. The product is characterized by high porosity and voidspace.

Figure 13A:
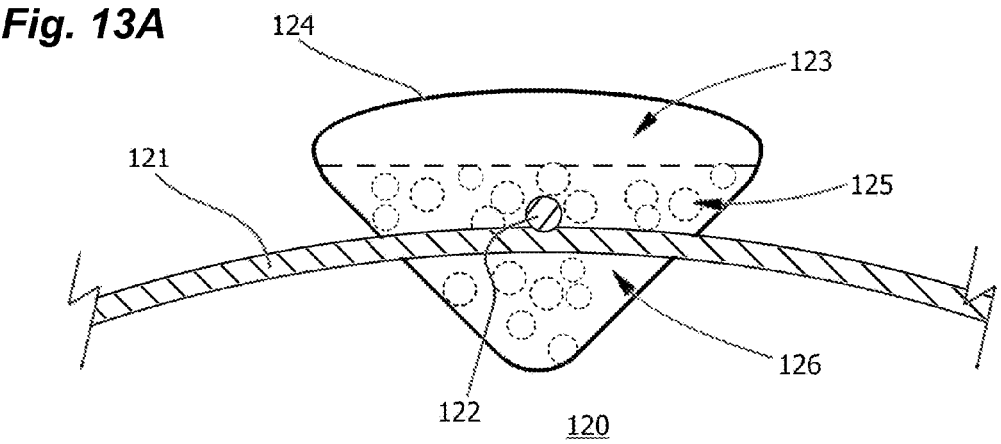
FIG. 13A is a sectional view of a float in which a hoop has been embedded.

FIG. 13A is a modified float (120), here shown in section to illustrate that a barrel hoop (121) and stave (122) has been embedded in the float. Again the reflective cap (123) is present and may be a coating. The upper layer (124) is buoyant. Under the upper layer is a body comprised of granules of mixed metal oxides (125) and a slow release clay matrix (126).

Figure 13B:
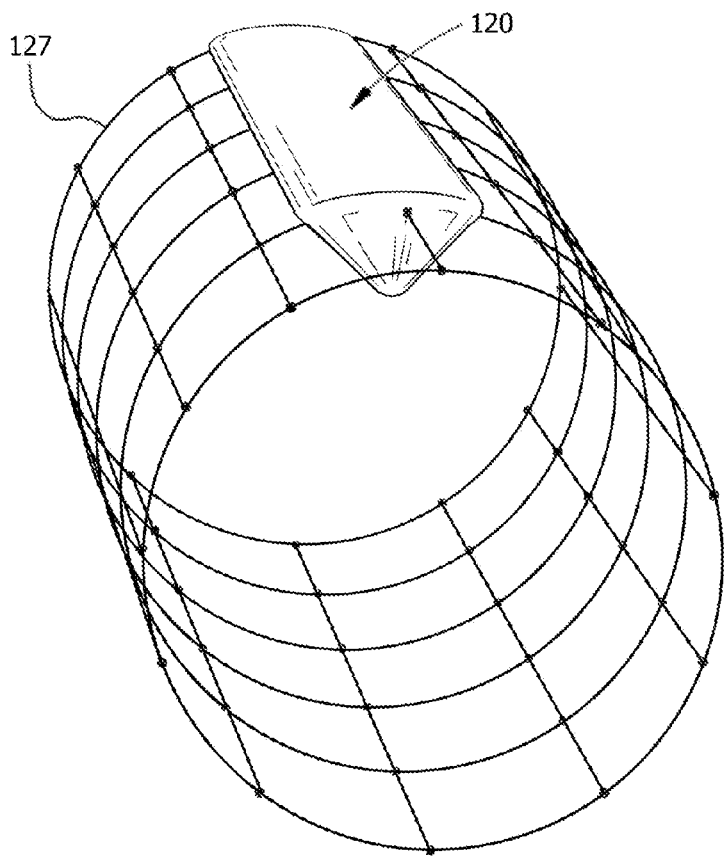
FIG. 13B is a perspective view of the float of FIG. 13A showing a wire barrel useful for providing intermediate habitat for complex ecosystems and multiple trophic levels.

This complex float is rendered as a complete structural unit in FIG. 13B. Here the float (120) is shown with embedded wire barrel (127), the wire barrel forming habitat for larger trophic levels, and a sort of pelagic nursery. The wire barrel also serves to prevent the floats from closing together in impenetrable poly-rafts. The float may be a meter or more in length if desired.

Figure 14A:
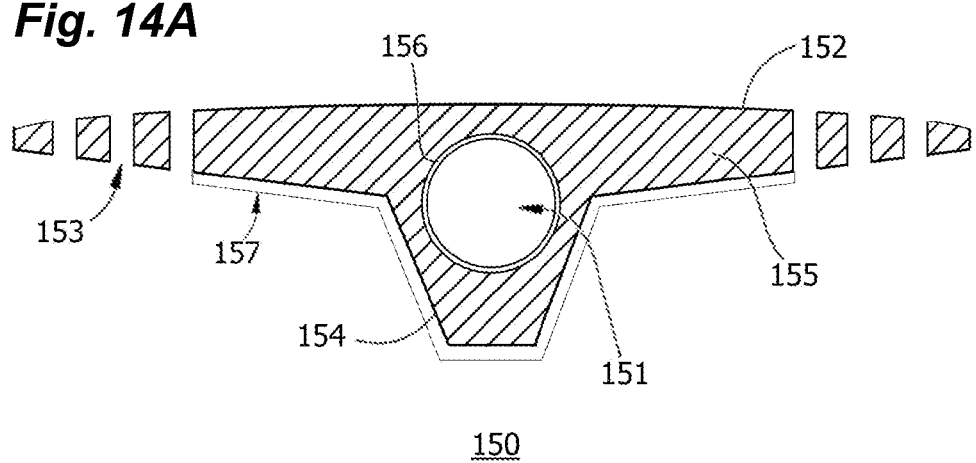
FIG. 14A shows an SRC formed as a large pontoon with reflective deck and keel piece.
Figure 14B:
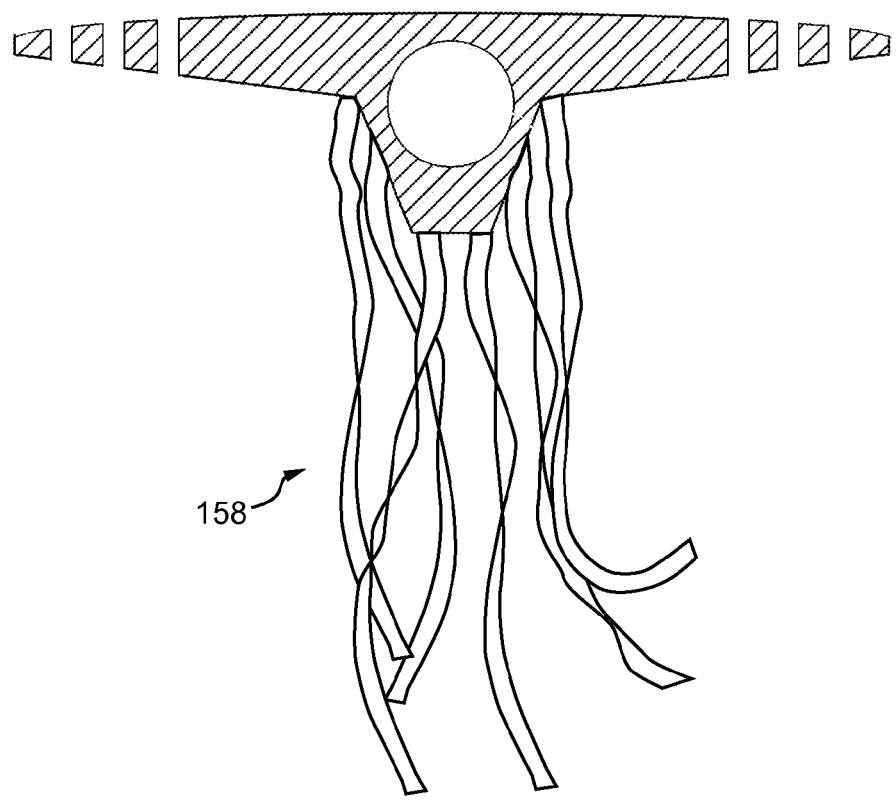
FIG. 14B shows an SRC with large pontoon festooned with hanging artificial kelp leaves providing intermediate habitat for complex ecosystems and multiple trophic levels.

FIG. 14A shows an SRC formed as a large pontoon with reflective deck and keel piece, and shows an SRC of several meters in width. This is a section through the structure of the pontoon; which is part of a larger structure forming a boom around a centrally anchored research platform. The boom may have a degree of flexibility while being relatively incompressible in diameter. In the center of the pontoon (150) is a hollow tube (156) that is filled with air (151) during surface operation. The top of the pontoon is a reflective surface (152) or coating, which may be periodically cleaned. The pontoon is perforated (153) to promote aeration during wave surge. A keel (154) is used for ballast. The core (155) is preferably a neutral density material. The rings are flexible so that the ring can undulate during passage of a swell. Optionally, an erodable anti-fouling coating (157) is supplied that contains an inorganic nutrient mix for supporting the growth of photosynthetic organisms and producing complex habitat. Erodable anti-fouling coatings need not be buoyant when applied to a floating pontoon or structure. FIG. 14B shows an SRC with large pontoon festooned with hanging artificial kelp leaves (158) providing intermediate habitat for complex ecosystem and multiple trophic levels, i.e., an artificial reef. The fill factor for supplemental habitat compositions on the ocean surface can be adjusted for effect.

As shown in FIGS. 6-14, the invention may include a buoyant composition for sequestering fixed carbon below the 100 year horizon of an ocean, for increasing marine biological productivity, and with reflective for increasing the albedo of a body of water. The composition comprises an inorganic nutrient or nutrients, generally in a formulation with balanced physiological ratio for supporting primary production of one or more food webs, in a sustained release solid matrix, the solid matrix having a light reflective surface or surfaces.

Turning to FIG. 15A, we see vertical spar buoy (130) configured to float with about 90% of its mass submerged relative to the waterline. The buoy comprises a hollow, elongate vertical body with superstructure (131) and ballast (132) assembly at the two ends joined in the middle by an elongate stem (133). The submerged understructure is a hollow tube with horizontal partitions in the upper levels and can be filled like a straw up to those partitions. The partitions separate an upper fixed displacement volume V1 and a lower variable displacement volume V2. Pumps are used to regulate the waterline, which is dynamically controllable. A self-propelled vessel that could be partially flooded at one end to assume this vertical posture was tested by Scripps Institute of Oceanography and found to provide a remarkably stable platform for oceanographic research that resisted pitch and yaw. Here the principle is adapted as a passive buoy for semi-permanent mooring on an anchored cable, and as will be shown below, combinations are introduced that build on this platform. Or the platform may be allowed to drift, such as in a gyre, serving as its own sea anchor.

FIG. 15B provides dimensions (in meters) for a structure of this class. Tubular construction with ferrocement, geocement, welded aluminum, or fiber-reinforced PVC forming the stem is contemplated, for example on a removable mandrel, from pre-shaped sections, or by shotcrete construction in a female mold using a track-mounted blower. In this model of the buoy, the total mass was $3.6 \times 10^6$ kg (assuming ferrocement), the displacement was $5.6 \times 10^6$ cubic meters of seawater, and the ballast mass on the bottom of the stem was $1.7 \times 10^6$ kg. This yielded a waterline about 17 meters from the top of the superstructure. The stem is partially flooded and the actual water line is controllable by controlling the level of water within the stem.

Figure 15C:
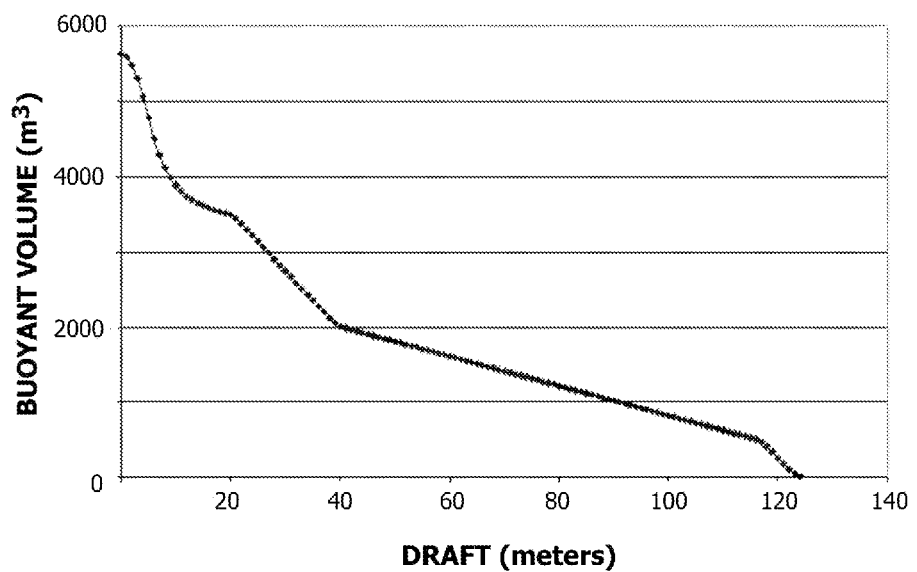

FIG. 15C is a plot of calculated displacement volume versus depth mark (draft) on a plimsoll. As would be expected, displacement volume increases from the ballast segment at the bottom of the structure (the 120 meter mark) and becomes maximal as the superstructure exits the waterline. The waterline is dynamic but is typically placed at the m mark. Cumulative total displacement at the 20 m mark is about 5600 metric tons as required for a heavy ferrocement structure. Lighter displacement designs using alternate materials are also feasible. Inertial forces causing the structure to sway laterally and to rise and fall in the surf are heavily dampened by the masses involved and the low overall center of buoyancy.

By use of internal structural partitions, a minimum waterline can be maintained. The structure is submersible. Submersion at a depth of 20 meters has an important advantage in weathering severe storms. It is assumed that the buoy will be anchored. The entire structure may be pulled down 20 meters under the ocean on a cable to ride out storm surges.

FIGS. 15D, 15E, and 15F depict a transverse and axial section of the buoy shaft 133. In transverse section FIG. 15E, the stem of the buoy from the sealed compartments to the ballast keel is seen to consist of a center void 142 in fluid connection with the ocean and a composite wall. The composite wall may include tubular reinforcements 143 embedded in a structural matrix 144. In a preferred embodiment, stainless or PVC tubing 143 is embedded in a ferrocement matrix 144. The outer layer 141 of the stem is generally a wound fiber such as a fiberglass designed to resist tensile deformation while the matrix of the wall itself is designed to resist compressive deformation. Optionally the inner wall may also be reinforced, but is generally smooth so as to permit easy cleaning by robotic sweepers. In axial section FIG. 15F, the inside waterline is shown to be adjustable by applying an air headspace so as to trim the buoy according to its ballast. The internal wall tubes are generally hollow and may be sealed at both ends to provide for permanent buoyancy, or one or more tubes may be open at one or both ends to provide cable housings, or small diameter seawater uptake tubulations such as for pumping deep water to the surface at higher velocity than would be achievable if the center void was the channel for upwelling (see FIG. 24). The smaller tubes may also be used to jacket yet smaller uptake tubes and provide for heating seawater so as to ensure it spreads on the ocean surface as a plume and does not sink as quickly as it is discharged at the surface if desired. Air lift pumping is also envisaged using internal plumbing of the kind illustrated here.

Figure 16:
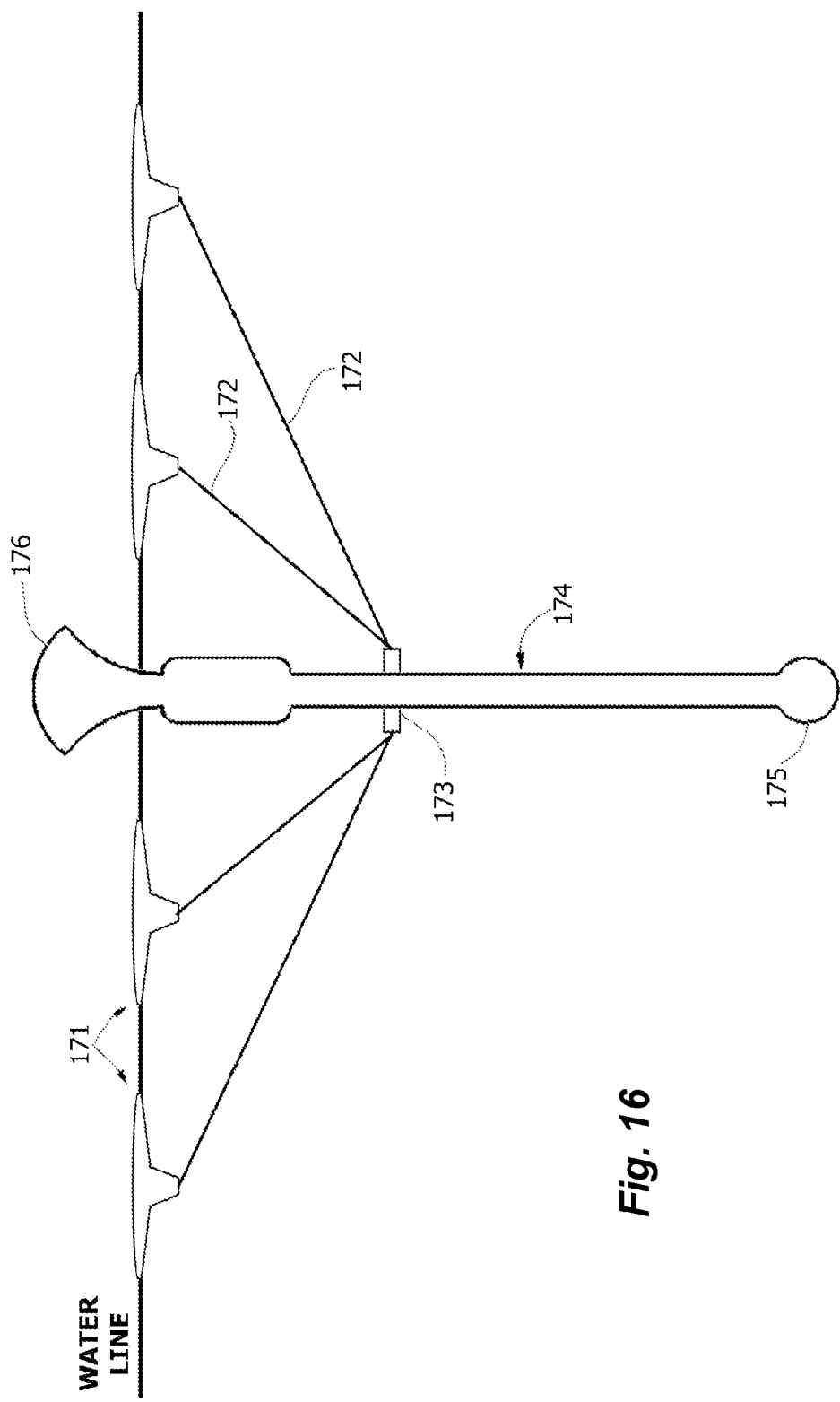
FIG. 16 shows a columnar buoy with outriggers.

FIG. 16 is a schematic of a single buoy with multiple boom platforms (171) at different diameters, held in place by nested cables (172). This form can be used to increase the reflective surface of the installation, and provides a large floating platform for pelagic aquaculture or research on carbon sequestration. In one embodiment, by mobilizing the collar yoke (173) on the central stem (174), fluctuations in the level of the outside rings do not result in excessive strains on the cable supports. Ballast (175) dampens oscillations of the buoy that would otherwise be associated with rough seas, so that the superstructure (176) remains level during transient fluctuations of the waterline.

Structures of this sort have a positive effect on local marine productivity. It is known that fish associate with floating objects (Hunter J R and C T Mitchell. 1966. Association of fishes with flotsam in the offshore waters of Central America. Fishery Bulletin 66:13-29); however, increases in primary productivity are greater than can be accounted for by clustering of schooling fish around buoys. SRC within the pontoon corral or "boom" result in a sustained bioavailability of trace minerals for primary producers and habitat and surface area for higher trophic levels without use of exogenous chelators. Sustained concentrations of iron(III) in the nM range, for example, exceed the $K_{sp}$ for iron in seawater—due to natural organic chelators released by organisms (see for example Kuma K et al. 1996. Controls on iron(III) hydroxide solubility in seawater: the influence of pH and natural organic chelators. Limn Oceano 41:396-407; Morel FMM and NM Price. 2003. The biogeochemical cycles of trace metals in the oceans. Science 300:944-47). Because biouptake controls the equilibrium between solubilized iron and the solid phase compositions, even elemental iron may be used as a source of iron in the SCR. Growth of biomass does not result in other elemental deficiencies secondary to consumption of iron because the formulations are typically supplemented with a full range of minerals in a balanced composition. The cables may have an elasticity in order that wear on rigid fittings is minimized, but rigid cables are also useable. Because tensile loads are distributed by multiple cables onto a reinforced ring of the buoy hull, little danger of simultaneous catastrophic failure exists.

Figure 17:
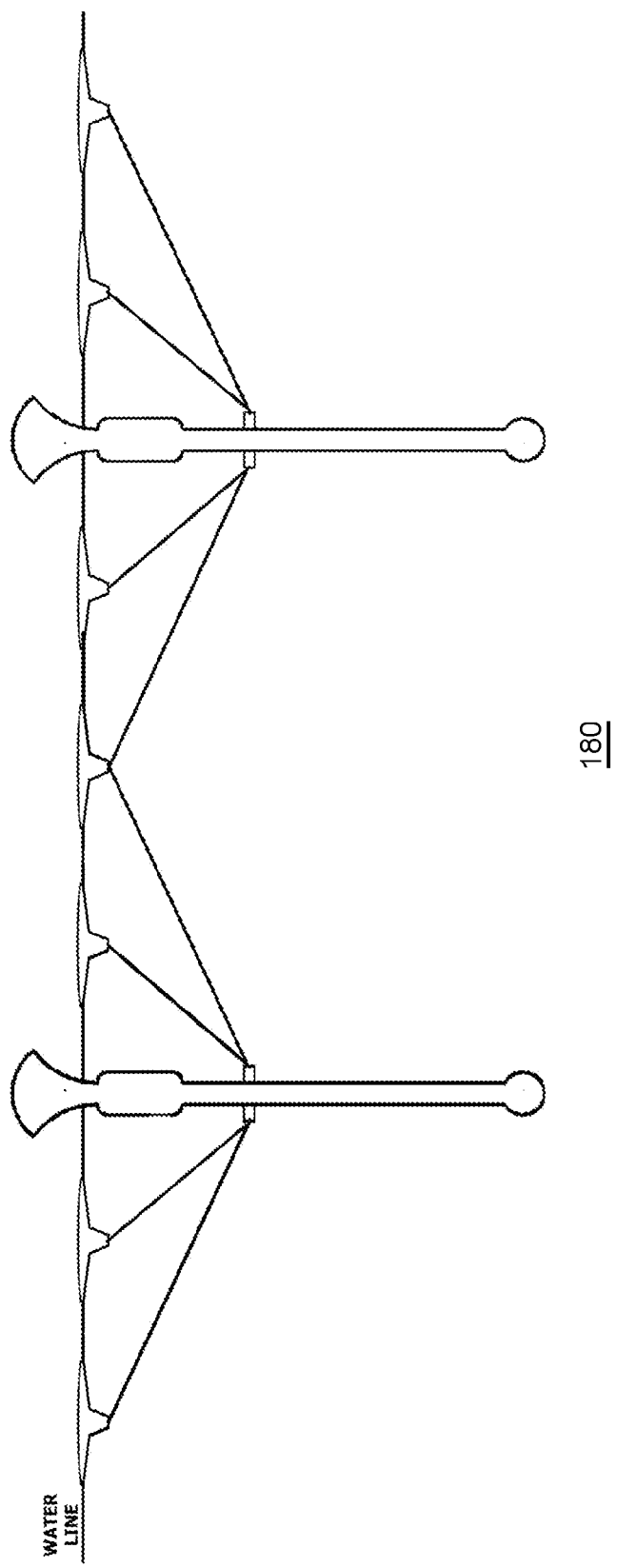
FIG. 17 shows a buoy array with nested circular pontoon booms.

FIG. 17 shows how the buoy platforms can be merged into planar arrays (180). By using large arrays, island-sized floating platforms can be constructed.

Figure 18:
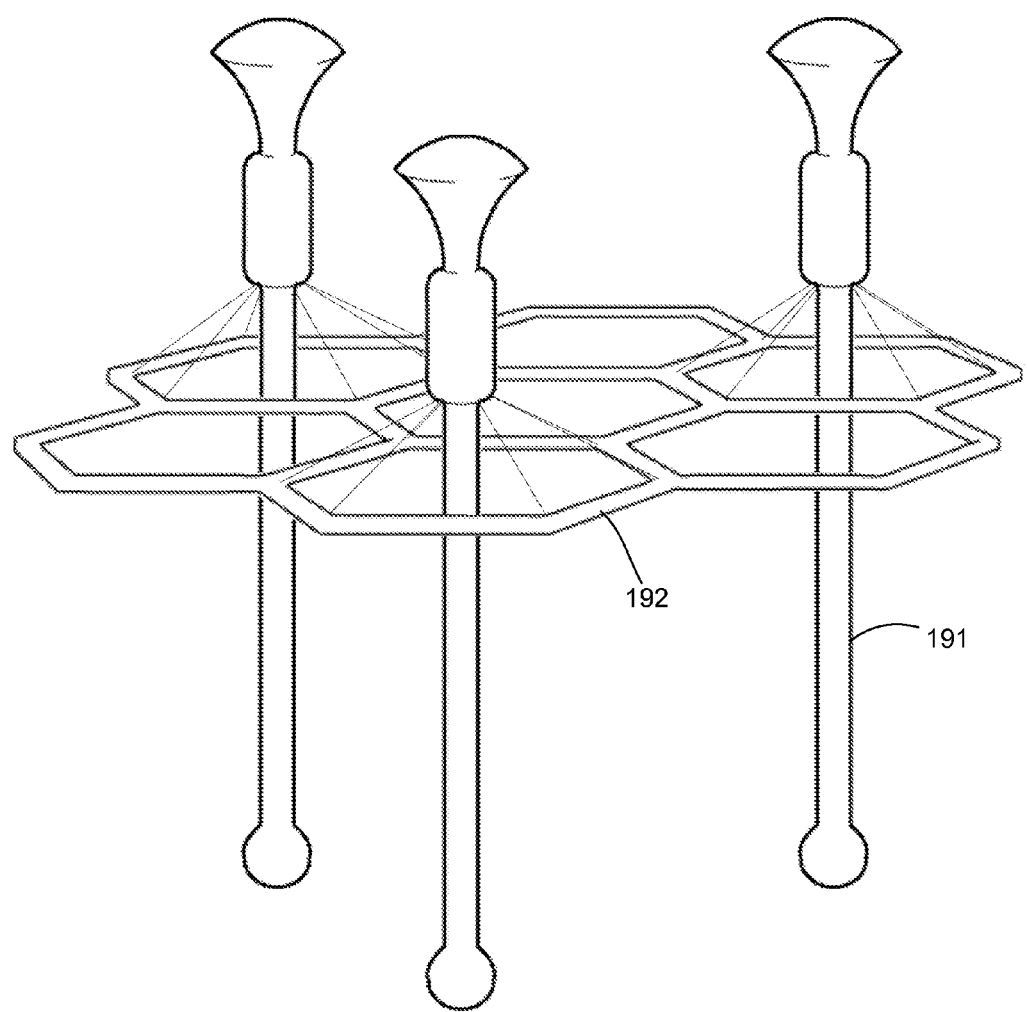
FIG. 18 shows a buoy network interconnected by cables joining a hexagonal planar submerged space frame.

FIG. 18 shows a buoy network (190) of spar buoys (191) interconnected by cables joining a hexagonal planar submerged space frame (192).

Figure 19:
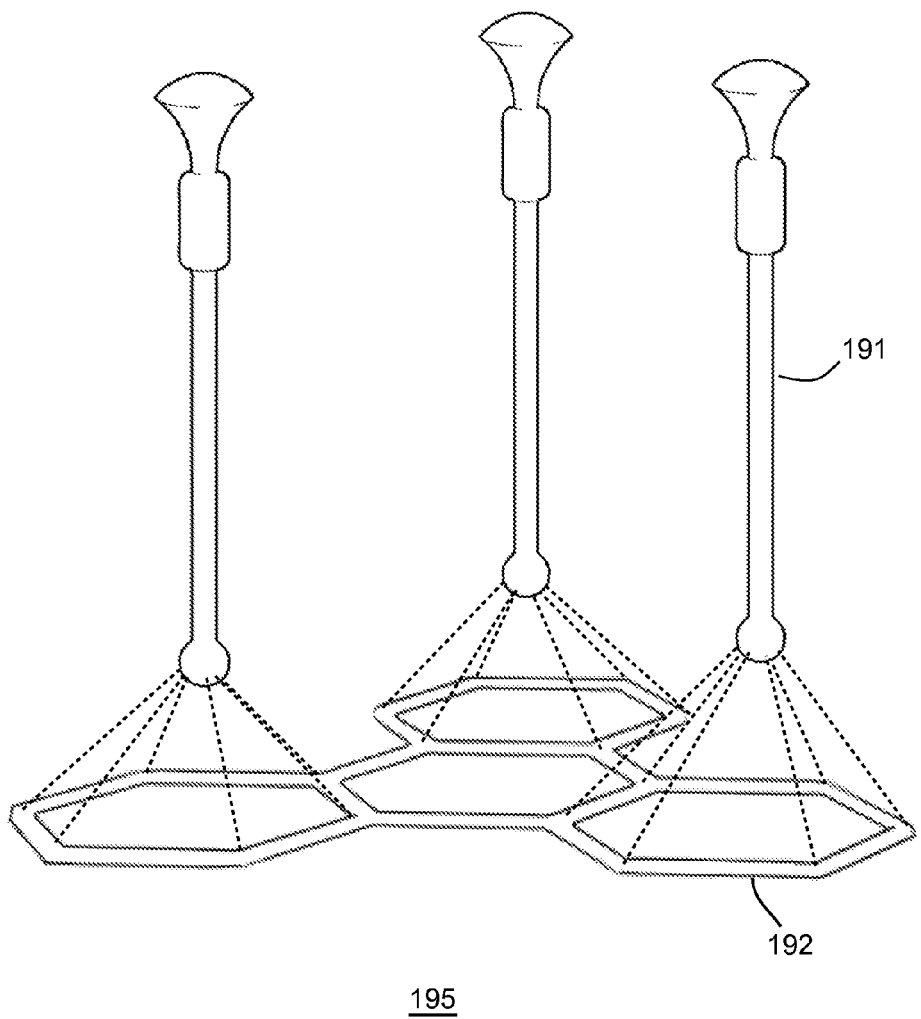
FIG. 19 shows a second buoy network interconnected by cables joining a hexagonal planar submerged space frame.

FIG. 19 shows a second buoy network (195) of spar buoys (191) interconnected by cables joining a deep hexagonal submerged space frame (192).

Figure 20:
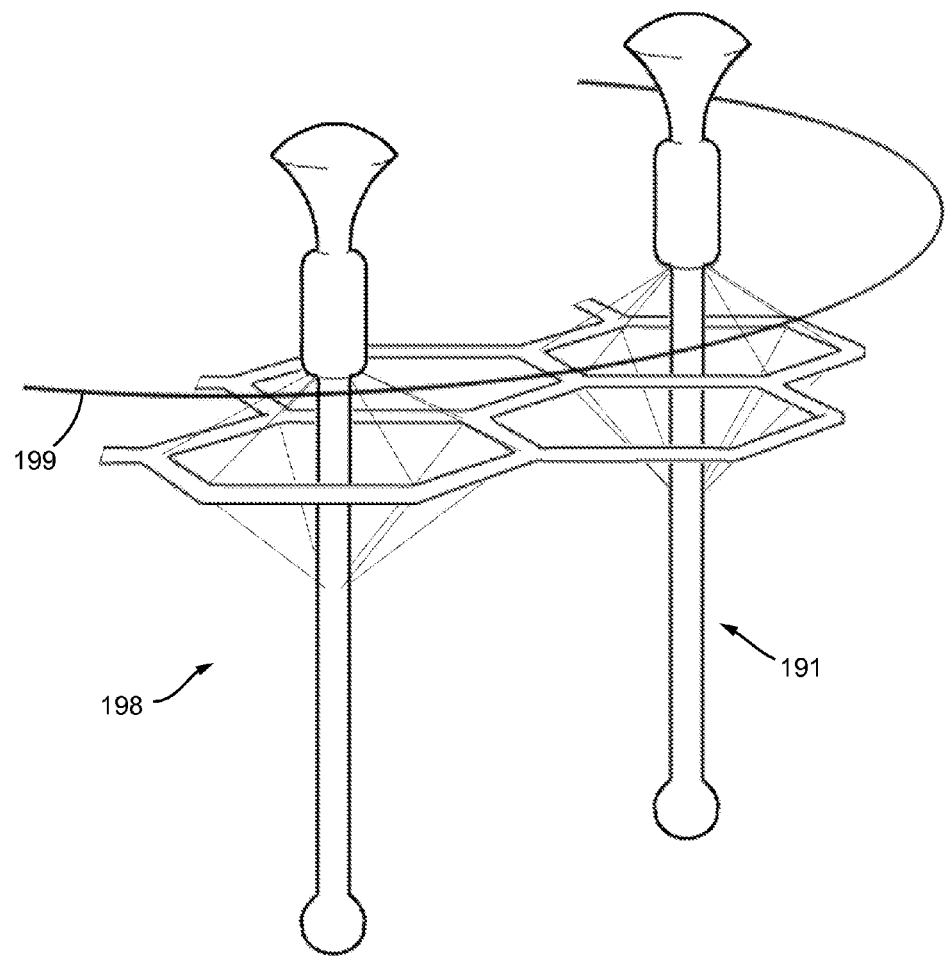
FIG. 20 shows a surface boundary defined by a buoy array or network having a submerged spaceframe for fixing the relative geometry of the buoys.

FIG. 20 shows a surface boundary (191) defining a surface area of an ocean. The boundary is defined by a buoy array or network (198) for fixing the relative geometry of the buoys. For research purposes the boundary encloses an area to be treated such that sedimentary carbon sequestration associated with that area will be measured. In this instance the enclosed area is an abstract mathematic concept useful in calculation primary productivity per unit surface area, and not requirely a physical boundary defined by a boom or some ocean fence.

FIG. 21 shows in schematic an integrated oceanographic workstation (200) with central spar buoy (201) with superstructure (202), ballast (211), and surrounding float boom (203) supporting, on suspended cables (204) from an adjustable yoke (205), a fully submerged and instrumented toroidal horizontal platform (206) at a level below the "100-Year Horizon", which by some accounts is 500 meters but can be reasonably approximated by a 100 m. The 100 Year Horizon is a depth at which organic matter, crossing that depth, is not likely resurface during the following century. The elevational dampening of the spar buoy (201) is engineered so that elastic or inelastic tensions on the suspension cables are within acceptable limits during a lifetime of up to 6 months or more. Multiplicity in the design accommodates progressive failure without loss of the instrument packages (207). Periodic cable replacement is assumed, preferably by bringing the instrument assembly and spaceframe up from depth for inspection and maintenance. As an alternative to a rigid toroid (206), a spaceframe of structural elements, for example a tensegrity structure or space-filling truss, can be used to form the horizontal platform. The purpose of the horizontal platform or spaceframe at depth is to provide a means for quantitating net sediment fall or "rain", including cell aggregates and faecal pellets, through the 100-year horizon and comparing this to gross productivity of the SRC-seeded body of water. Samples of the particle sediment are analyzed for fixed carbon in order to validate carbon sequestration per unit time and to study diurnal or seasonal variations, or the effect of experimental parameters such as nutrient supplementation. A horizontal plane (210) forms the "sampling grid" or "transect line". In one embodiment, a fine mesh plankton net is stretched across the frame of the toroid, and robotic strainers vacuum up the filtrate at regular time intervals. In another embodiment, lasers and photodiode detectors are used to quantitate particle transits per unit time and particle size in the manner of a particle counter. A field of criss-crossing laser beam particle counters is conceived. Violet blue lasers (e.g. 465 or 472 nm) and green lasers (e.g. 532 or 543 nm) are useful and are selected here because the transparency of water in this wavelength range is reasonably good. Light in the laser beam is scattered by particles intersecting the beam; the time and scattering coefficients correlate with the size of the particle. Stacked spaceframes at different depths are also conceived. By linking multiple buoys together on the surface, the spaceframe can be suspended at multiple attachment points, permitting higher confidence in the determination of sediment fall parameters over the full grid area encompassed by the spaceframe, independent of ocean currents. The annular pontoons also act as wave dampeners for the central spar, increasing stability.

Outriggers are used to anchor a tubular barrier float boom or ring-like pontoon around a defined surface area of water. SRC are dispersed within the encircling float boom. The outriggers are collapsible and can be drawn up during storms. Gantryways give access out to suspended nets where samples can be taken. A laboratory for sample processing and measurement is provided on an upper deck, with access to a pump room. The pumps are used to control the level of the waterline. An upper observation deck or solar panel installation (212) is mounted above the superstructure along with egress to the gantryways. An antenna (213) with communications device is mounted so that data may be streamed to satellite transceivers during automated operation.

The buoy serves as both a marine productivity island and an instrument platform. The superstructure may be configured for aquaculture, aquacultural research, or for validation of sedimentary carbon sequestration. This apparatus is useful in a variety of methods which are further embodiments of the invention. Methods of the invention include a method for sequestering fixed carbon below the 100 year horizon of an ocean, which comprises dispersing a buoyant composition on the surface of the ocean, the buoyant composition comprising an inorganic nutrient or nutrient formulation in an inorganic sustained-release matrix, and a light reflective surface or cap that tends to orient itself skyward when floated. Also conceived is a method for increasing planetary albedo by dispersing on the surface of an ocean a composition having a light reflective surface and optionally an inorganic nutrient or nutrients in an inorganic sustained release matrix.

In another aspect, the compositions and apparatus of the invention more generally are representative of compositions and apparatus for quantitative solar exsolation, where the amount of exsolative energy transferred from the terrestrial surface to a plane above the troposphere (generally taken as the layer of atmosphere extending from the earth's surface to the base of the stratosphere, about 10-16 km above the earth and marked by decreasing temperature as a function of altitude) is quantified and validated. By validating the energy flux or flux rate, for example in units of Joules or Joules per unit time, exsolation credits may be issued. Exsolation credits are financial instruments tied to a specific unit of energy transferred from the earth's surface to a plane above the troposphere, or more preferably above the stratosphere. The amount of energy transferred may be validated by satellite pyrometry or by mathematical modeling based on measurement of a terrestrial reflection and properties of the atmosphere in the path of the reflected light.

Exsolation credits are disbursed or traded, for example in a commodities market. A market for trading a solar exsolation credit instrument issued by the above apparatus will generally include a computer, the computer comprising a microprocessor, a volatile memory, a non-volatile read-only memory containing instructions for the microprocessor, a database containing records, the records comprising an ask price for a solar exsolation credit instrument and a bid price for a solar exsolation credit instrument, and a user interface for entering and displaying said records. The computer is generally programmed also to execute trades. Optionally a communications port is provided for remotely displaying ask prices, entering bids and confirming trades, as is generally familiar to those familiar with modern commodities markets. However, a market for a commodity, where the commodity is a heat transfer unit, is not a conventional market, and is useful to more fully assess the relative distribution of resources and labor between processes where the social benefit needs to be balanced against a heat output or a greenhouse gas output into the common atmosphere. For example, a process that results in conversion of a higher albedo surface to a lower albedo surface may not be commercially attractive if the total costs of global warming are added to the project; and by placing a cost on an equivalent discharge of heat from the terrestrial surface, the operator of the process has the option of ameliorating the damage only to the extent that the value of the product of the process exceeds the cost of the amelioration. And in this way, processes competing for exsolation credits are brought into a zero net sum market, which is required to be sustainable. Unsustainable processes that result in more heat than is balanced by available exsolative credits will not be profitable and will cease. A market for exsolative credits may be modeled on a "cap and trade" system for carbon credits, and is complementary thereto.

Similarly, a process that results in greenhouse gases can give rise to a trading system for ameliorating carbon emissions at a cost to the producer. A market for trading a solar exsolation credit instrument issued by the above apparatus will generally include a computer, the computer comprising a microprocessor, a volatile memory, a non-volatile read-only memory containing instructions for the microprocessor, a database containing records, the records comprising an ask price for a solar exsolation credit instrument and a bid price for a solar exsolation credit instrument, and a user interface for entering and displaying said records. The computer is generally programmed also to execute trades. Optionally a communications port is provided for remotely displaying ask prices, entering bids and confirming trades, as is generally familiar to those familiar with modern commodities markets. Again the result is a selection pressure favoring sustainable processes. Not only must the social costs of greenhouse gas production and release be considered, but the global heating and cooling balance must also be considered in tallying social costs of processes, industries and markets that release greenhouse gases. A "cap and trade" system for carbon credits is useful for monetizing carbon sequestration certificates for example.

Many national strategies seek to limit the rate of growth in the amounts of atmospheric greenhouse gases by emissions trading. Emissions trading is a process whereby specific target emission rates of for example carbon dioxide are set for specific industries. A member of the industry who achieves measured emissions below the target rates may trade the difference on the open market to another who fails to achieve its emission targets. An entity responsible for measured emissions above its target rates may be subject to fines or other sanctions. The objective is to reduce the overall emission of greenhouse gases in the atmosphere, even if the emissions of one particular source are not decreased, or indeed are increased, by ameliorating that environmental damage while giving industries time to adapt and phasing out uncompetitive processes and plants. In the last decade, the effectiveness of this market-based emissions reduction approach as applied to criteria air pollutants in the US has been demonstrated. However, for those industries hard hit to adapt, carbon sequestration certificates resulting from the apparatus and methods of the invention may be made available on an open market to as to prevent short-term job and investment loss.

The unit of measure of tradable carbon emissions that has been generally accepted is commonly known as the Carbon Emission Reduction Credit, or CERC, which is equivalent to one metric ton of carbon dioxide gas (or other greenhouse gas equivalent) that is not emitted into the earth's atmosphere (emission reduction) or one metric ton of carbon dioxide that is removed from the atmosphere (emission offset) due to a human-caused change. That is, a CERC can be generated for human activities that have occurred since a base year, e.g., 1990, that have resulted in a reduction of business-as-usual emissions of greenhouse gases.

A market is emerging for trading CERCs, EBCs and other green tags. For example, CERCs can be generated through energy efficiency gains of fossil fuel technology, substitution of biofuels for fossil fuels, or removal of greenhouse gases from industrial gas streams. CERCs also can be generated by sequestration of atmospheric carbon dioxide into the ocean as described in the present disclosure, including the drawings and the claims.

FIG. 22 describes a method for issuing validated carbon sequestration as part of remedial geoengineering to remove excess $CO_2$ from the atmosphere. In a first step an array or network of spar buoys is deployed to define a bounded surface area where ocean chemistry and habitat surface area will be modified to increase primary productivity. A buoyant inorganic composition is dispersed within the study area, the composition having a topology with microscopic and macroscopic niches for supporting a complex trophic system. Suspended from the network or array is a space frame defining a 100 Yr horizon such that sedimentation through the space frame will be detected and is representative of fixed carbon that has been effectively removed from the atmosphere for at least a century. The instrumentation for detection of particle sediment is generally mounted on the space frame, and for example can include photodetectors and laser beams for detecting falling particles. Total sedimentation is integrated as sedimentary deadfall per unit time to validate the flux of sequestered carbon crossing the 100 Yr horizon and one or more monetizable or tradable carbon sequestration certificates are issued accordingly.

Figure 23A:
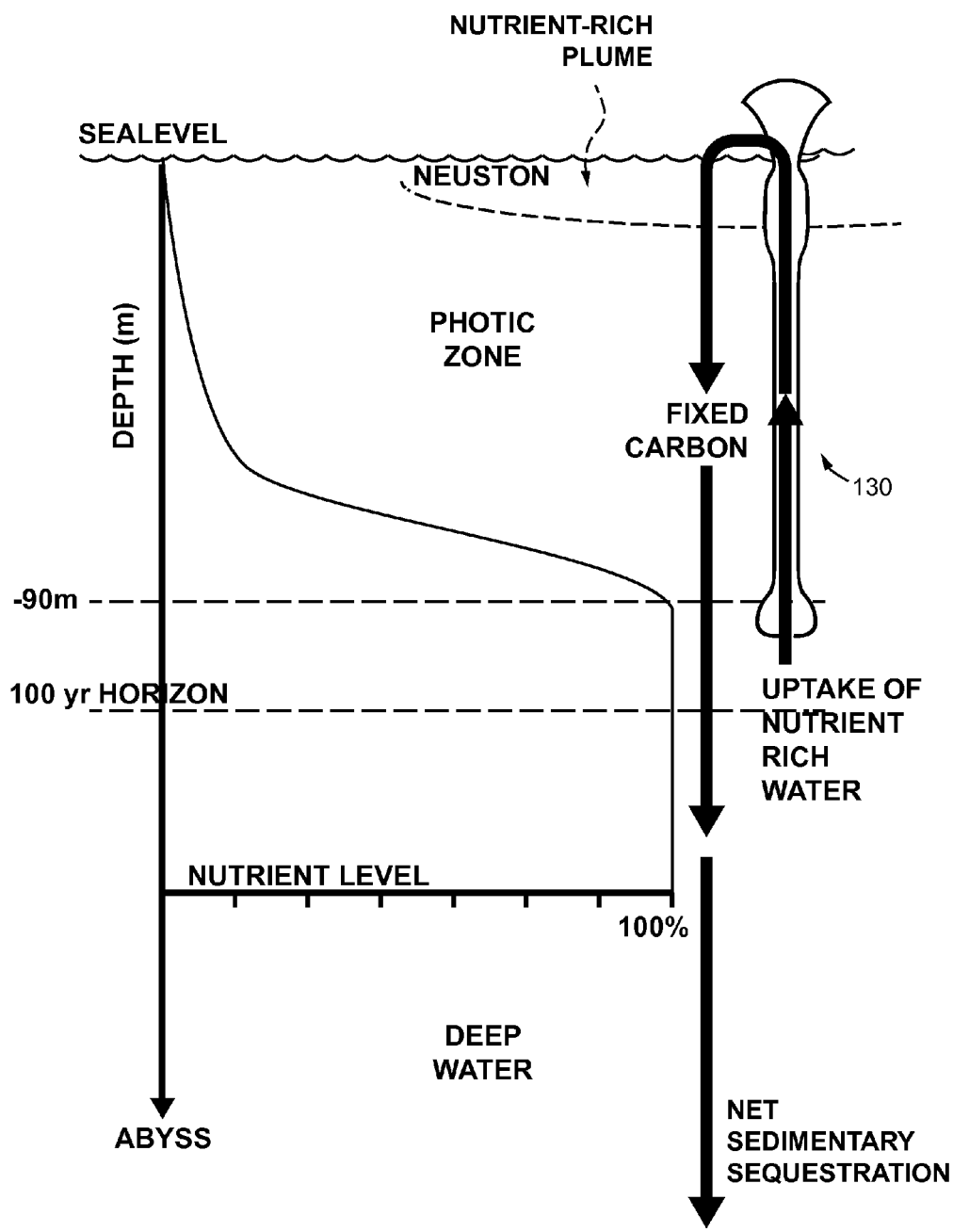
FIG. 23A is a schematic view of a column of water showing use of the spar buoy apparatus of the invention to fertilize the photic zone by circulating deep water to the sea surface. Nutrient rich water brought to the surface will admix with nutrient poor surface water, increasing biomass and fixed carbon flux falling below the 100 Yr horizon (biological pump). A plot of nutrient level relative to the photic zone is shown.

FIG. 23A is a schematic view of a column of pelagic water showing use of the spar buoy apparatus (130) of the invention to fertilize the photic zone by circulating deep water to the sea surface. Nutrient-rich water brought to the surface will admix with nutrient-poor surface water, increasing biomass and (at steady state) the flux of fixed carbon falling below the 100 Yr horizon (biological pump/down arrow). The apparatus is generally placed in the open ocean where ocean depths are greater that two or three thousand meters. This ensures that rapidly sedimenting large fecal pellets will reach bottom in one or two days, essentially undigested by mesozooplankton.

In this view, deep water is shown to rise under pumping action within tubulation associated with the spar buoy and to be discharged at or near the surface, forming a nutrient-rich plume that spreads on the surface and fertilizes the neuston. The pumping action is powered by sustainable energy sources known in the art, such as a solar collector or a windmill. Advantageously, mixing devices such as sprayers may be used to avoid the frequent surface sedimentation that results due to falling rain. Also of interest is salinity and temperature, which can control the sinking (or floatation) of the plume.

A plot of nutrient level relative to the photic zone is shown. Nutrient levels are generally very low close to the surface and in the photic zone, but increase to essentially a plateau below a depth of about 90 meters or less, depending on turbidity.

Figure 23B:
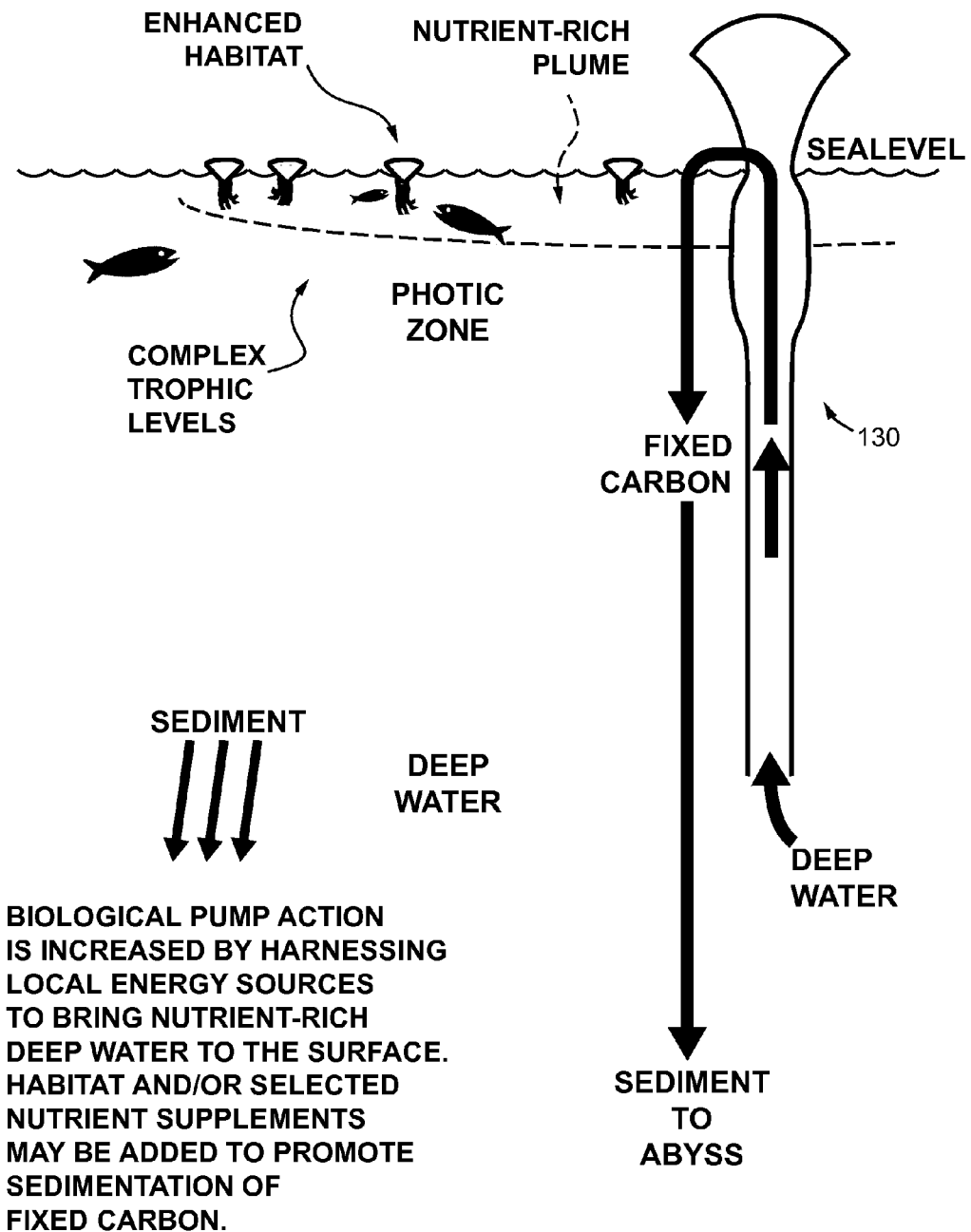
FIG. 23B is a detail view illustrating effects of a habitat-enhanced surface plume of nutrient-rich water on trophic levels and sedimentation rates at the surface of an oligotrophic ocean.

FIG. 23B is a more detailed view illustrating effects of a habitat-enhanced surface plume of nutrient-rich water on trophic levels and sedimentation rates at the surface of an oligotrophic ocean. The presence of a habitat-forming composition supporting higher trophic levels significantly increases the size of sedimentary particles. Whereas picoplankton give rise to a marine snow and opal of microscopic sizes, large copepods and predators give rise to sediment that falls one or two thousand meters per day, ensuring that most reaches the abyss without significant regeneration of inorganic carbon. The speed of descent is also favored by more dense materials, such as coccolith pellets produced by coccolithophorids and calcium carbonate shells produced by foraminifers.

Habitat enhancement using habitat-forming compositions is conducted in such a way as to avoid high fill factors that would reduce gas exchange. FIG. 13B illustrates one way to prevent the fill factor from approaching unity. FIG. 16 suggests another, where supplemental habitat compositions are dispersed in the area between the outer boundary rings. Spraying upwelled water over a large surface area of the ocean may also be used to maximize $CO_2$ uptake by primary producers. Avoiding excess nutrient concentration will also limit eutrophic conditions, and the invention includes the teaching that habitat-rich compositions may be effective absent supplemental nutrient compositions because of the effects of solid substrate surface area and niche diversification. Habitat enhancement refers to the provision of solid substrate surface area having microscopic and macroscopic niches in a fractal scalar range of sizes that promote formation of multiple trophic levels and food chains, food chains that include larger predators, harvestable fish, crabs and shellfish. In a preferred embodiment, the apparatus serves as an artificial reef having daily primary productivity of 1 to 3 gm $C/m^2$/day. Shown here within a defined area around the spar buoy (130) are floating pontoons such as were featured in FIG. 14B, having kelp-like stringers that support fish nurseries and a myriad of microscopic plants and animals. This increased surface area also has a dramatic effect on nutrient chemistry, both by increasing the amounts of native chelators, and also by trapping nutrients in inorganic and organic form on solid surfaces so as to prolong recirculation through the biological food web. In a preferred embodiment, a steady supply of deep water supplied to a habitat-enriched artificial community results in a dramatic increase in oligotrophic epipelagic waters, up by a factor of about $10^3$ from baseline per unit surface area. At steady state this production results in sedimentary deadfall, and by use of habitat compositions, efficiency of sedimentary deadfall in depositing fixed carbon on the ocean bottom can be increased by about ten-fold.

Figure 24:
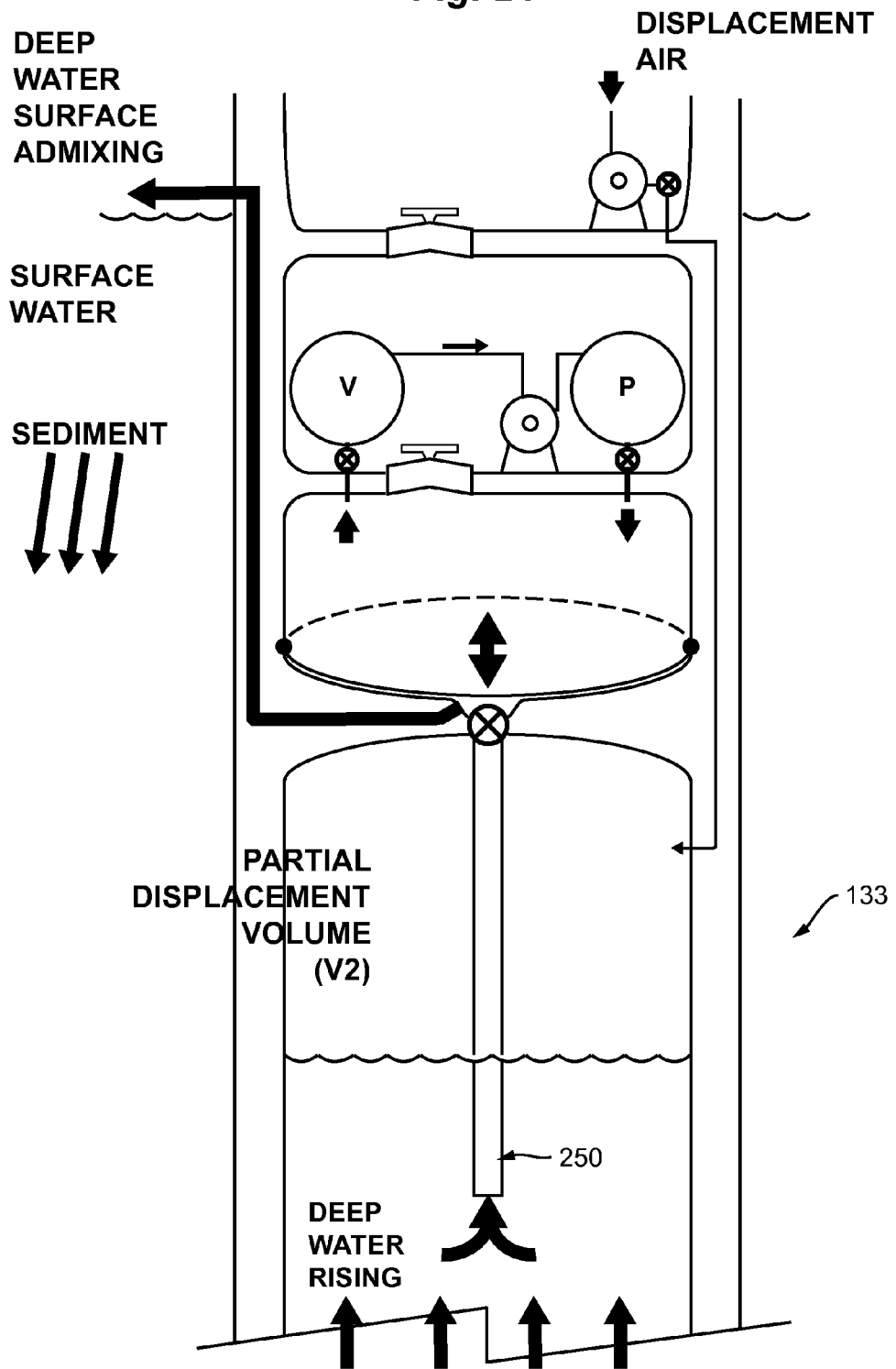
FIG. 24 is a model of a diaphragm pump for drawing deep water to the surface. The diaphragm is drawn to emphasize the simplicity of the apparatus.

FIG. 24 is a model of a diaphragm pump for drawing deep water to the surface. The diaphragm is drawn to emphasize the simplicity of the apparatus. Shown here is a section of the stem of the spar buoy (133) showing the partial displacement tube (bottom) and the sealed compartments of the working buoy. A vacuum tank (V) is used in the fill stroke, and an accumulator or pressurized tank (P) is used for the discharge stroke. Compressed air is pumped from the vacuum tank to the accumulator tank using a pump and a series of valves. Water discharged from the diaphragm pump chamber exits the spar buoy at or near the surface. The hydrostatic pressure head is essentially zero, and thus the volume per unit time may be large without requiring much energy. Deep water enters the diaphragm pump assembly through draft tube 250. The energy required for driving pumping may be obtained as solar energy, or most preferably from wind, for example. While this compressed air-driven diaphragm pump is designed for a stroke volume of almost 100 m$^3$/stroke, smaller diaphragm pumps may also be used. Centrifugal and piston pumps are also envisaged and run using sustainable energy sources drawn from the local environment in the open ocean.

Also shown are pumps for maintaining trim relative to a defined waterline. The partial displacement volume (V2) may be adjusted to control the waterline of the buoy and/or even to provide complete immersion as described below with reference to FIG. 28. Hatches provide entry to the fixed displacement volume areas as needed. In this view, deep water rises in the center tube, but concentrically arranged tubes such as shown in FIG. 15E may also be used to increase the pumping flow velocity and prevent excessive residence times in the tube, which can lead to colonization of internal surfaces; colonization that would require periodic maintenance to remove.

Figure 25:
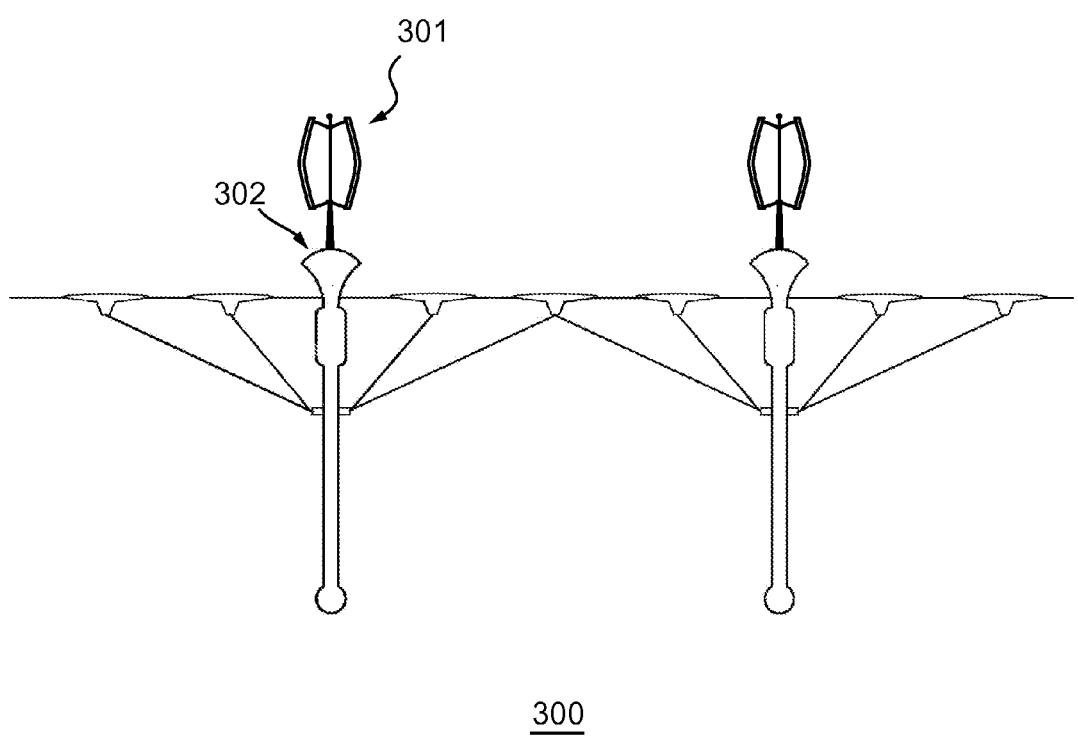
FIG. 25 is a schematic view of an array of stabilized vertical buoys with windmills mounted on spars, the windmills providing renewable power for pumping nutrient-rich water to the surface.

FIG. 25 is a schematic view of an array (300) of stabilized vertical buoys with windmills (301) mounted on spars, the windmills providing renewable power for pumping nutrient-rich water to the surface. Windmills of this type are resistant to strong winds but optionally may be collapsed during gales or high seas. Renewable energy may also be supplied by solar panels (302) mounted on the superstructure of the spar buoys.

FIG. 26 diagrammatically outlines steps in a method to continuously supply nutrients to the upper water layers and neuston so as to increase biomass and net carbon sequestration. Habitat supplementation may be provided to ensure higher trophic levels most associated with large carbon flux at steady state, where community flux out equals exceed nutrient flux in. Nutrient rich water is pumped through the spar buoy and discharged at or near the surface. Adjustment of salinity or temperature may be performed as desired. The nutrient supplementation promotes primary productivity in the photic zone and results in an increased sedimentary deadfall. Instruments mounted on a space frame near the bottom of the spar buoy detect and quantitate the falling particles. A flux in units of fixed carbon per unit time is measured and validated. Carbon sequestration certificates are then issued according to the measured carbon flux below the 100 year horizon. This is a continuous process driven by locally-produced renewable energy. Habitat supplementation may include nutrients. Limiting nutrients may be supplied, or nutrients not limiting but provided in excess so as to shape the kind of community that becomes established so as to promote certain kinds of mineralization of carbon, for example.

This is an elegant solution to the dilemma of the IRONX experiments, where supply of one limiting nutrient creates a downstream plume of waste water that is deficient in all other nutrients, essentially robbing other patches of water of productivity so as to increase productivity within a defined area.

Figure 27:
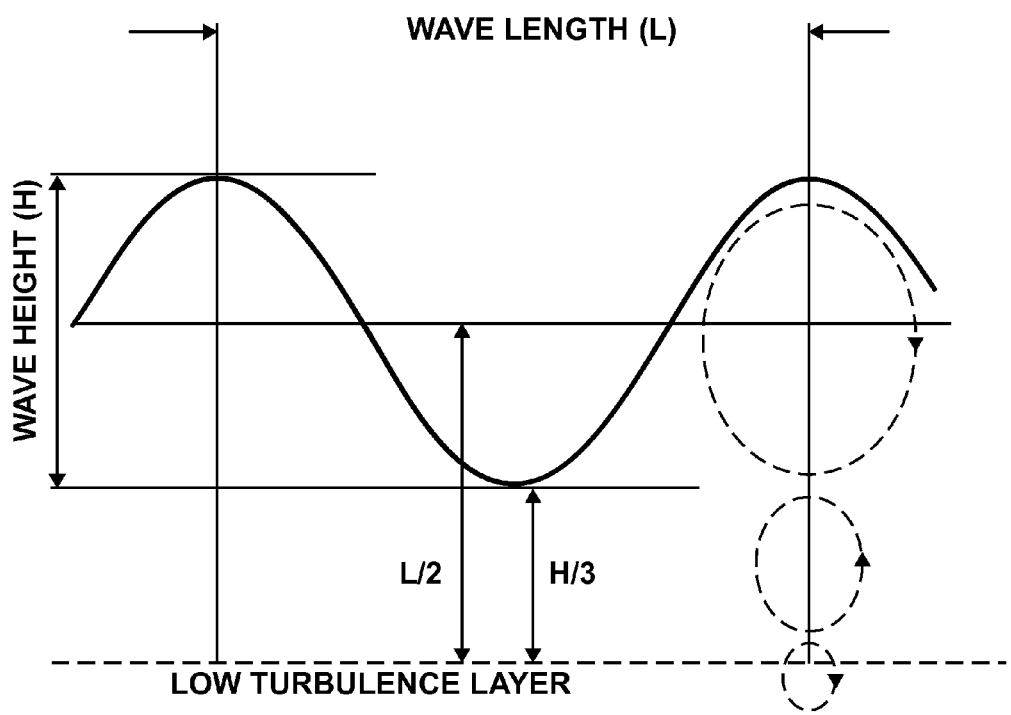
FIG. 27 defines commonly cited parameters of wave geometry, and rules of thumb for calculation of depth at which turbulence is substantially reduced.
Figure 28:
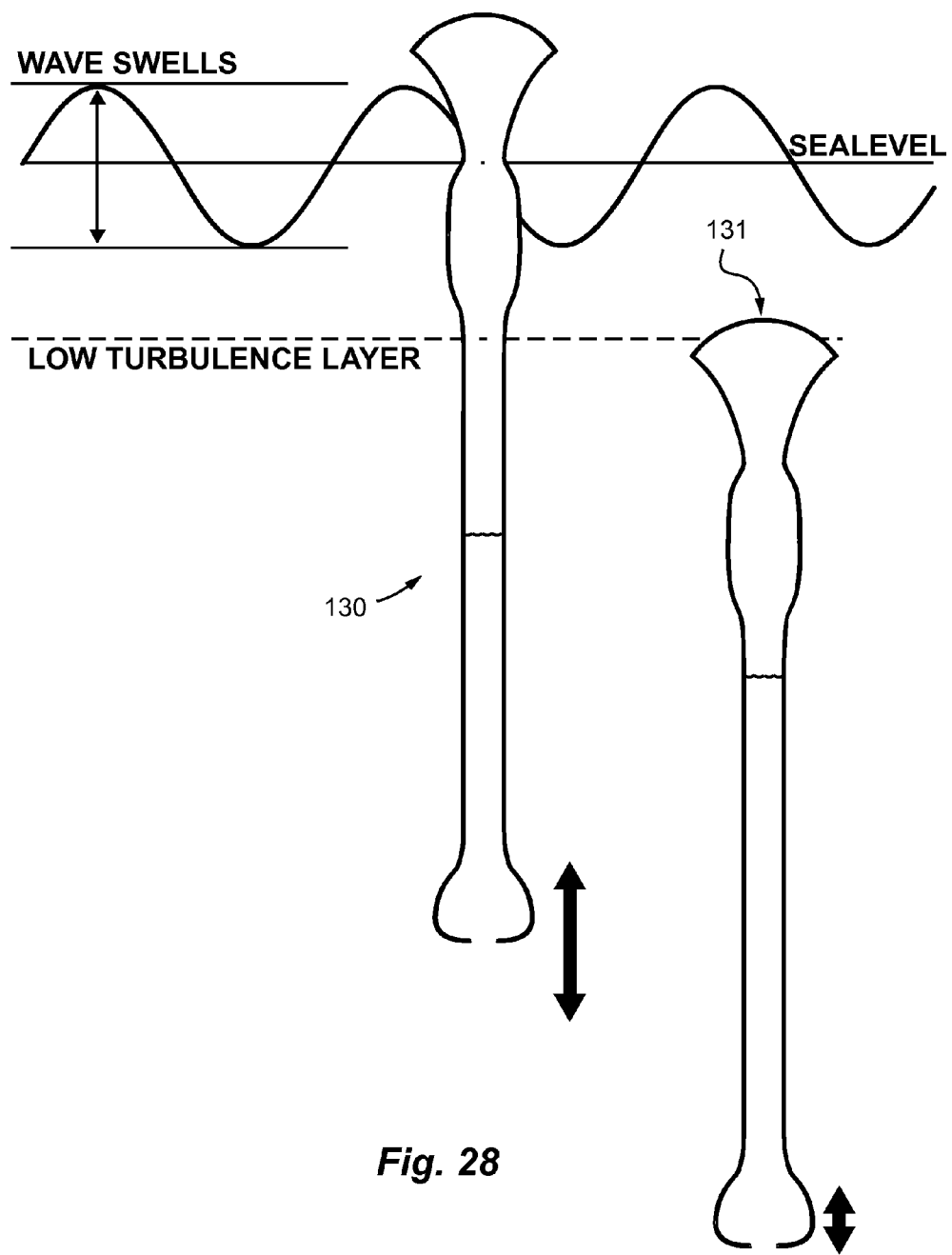
FIG. 28 demonstrates that partial submersion of the apparatus can result in a state in which there is essentially no vertical oscillation.

FIG. 27 defines commonly cited parameters of wave geometry, and rules of thumb for calculation of depth at which turbulence is substantially reduced. In deep water, the orbital motion of a fluid particle in the advancing wavefront is rapidly dampened with increasing depth, and can generally be neglected at half the wavelength (L/2) or at one third the wave height (H/3). Wave power is generally described in kW per meter of wavefront and may range from 0 to 50 or more kW/m, sufficient to pose a structural hazard. However, a low turbulence layer exists immediately below the surface of the open ocean, and submersion of an apparatus of the invention into that low turbulence layer by adjusting the variable displacement component (V2) protects the apparatus from major damage in heavy storm surge or violent winds. The concept is shown in FIG. 28, which demonstrates that partial submersion of the spar buoy (130) can result in a state in which there is essentially no vertical oscillation (small double vertical arrow) whereas surface exposure is associated with oscillations at a harmonic of the wave periodicity (large double vertical arrow). The top end and superstructure (131) of the spar buoy is designed to seal for this application, and the positive displacement volume ensures a generally neutral density. The large dampening mass at the keel of the buoy is also effective in dampening surface oscillations, even at the surface, and also serves as a sea anchor. Alternatively, the apparatus can be submerged using winches anchored to cables on the seafloor or seamounts. Either way, a 20 m or 30 m wave height is withstood by designing the device to submerge below the turbulent upper layer when needed. Interestingly, at a submersion of 30 m or more, the apparatus is also capable of avoiding damage due to collisions from errant shipping traffic.

EXAMPLES

Example 1

A 30 mL aliquot of a 10% (w/v) stock of Miracle-Gro (Scott's Miracle-Gro Products, Marysville Ohio) was added to 50 mL of colloidal silica in methanol (Nissan Chemical America, Tarrytown N.J., CAS 112926-00-8) and the mixture was heated in an open vessel to reduce the volume to about 40 mL. A clear solution resulted. The solution was then allowed to cool and a clear hard gel matrix resulted. Over time in an open container, a somewhat brittle solid formed.

A binder such as a sol-gel precursor is optionally used to semi-permanently fuse the colloidal silica, as is done in silica "hardcoat", a commercial process (see for example U.S. Pat. No. 6,587,263). Entrained air or $CO_2$ is also incorporated in the matrix.

Example 2

The following mineral components were crushed and mixed with a mortar and pestle.

| Major Inorganic Species | gms |
| --- | --- |
| Iron Oxide | 50 |
| Iron Nitrate | 10 |
| Calcium Oxide | 20 |
| Calcium Phosphate | 10 |
| Zinc Carbonate | 5 |
| Magnesium Oxide | 4 |

To 10 gm of the above mixture, the following trace mineral components were added with further grinding.

| Trace Inorganic species | gms |
| --- | --- |
| Copper Nitrate hemipentahydrate | 0.70 |
| Phosphomolybdic Acid | 0.20 |
| Manganese Chloride | 0.08 |
| Phosphomolybdic Acid | 0.01 |
| Cobalt Nitrate hexahydrate | 0.01 |
| Boric Acid | 0.005 |
| Selenium Chloride | 0.001 |
| Sodium Vanadate | 0.001 |

To this mixture of solids, 200 mL of colloidal silica in methanol was added. After heating with stirring to reduced volume and cooling, a hard gel formed. This gel when baked produces a rock-like composition without the decomposition indicative of organic charring.

Example 3

As a first approximation, mix the aqueous suspension of Example 2 with 200 mL of colloidal silica in methanol as described above. After heating with stirring to reduced volume, add 300 gm of glass hollow microspheres and continue stirring until fully mixed. Charge 50 mL iron molds with the mixture, the molds having a selected shape and depth, with a shallow conical bottom profile. Bake to lithification.

During the early stages of baking, it is anticipated that the iron filings will sediment to the tip of the base of the mold and the glass hollow microspheres will rise to the surface of the liquid. This results in a "puck" shaped siliceous ingot on ejection from the mold. The ingot is comprised of highly dispersed inorganic minerals, sedimented iron filings, and a froth of microbubbles in a silicate matrix. In other words, puck density is here preferably non-uniform but is cumulatively less than that of water, that is to say the aggregate density is less than 1 $gm/cm^3$. By optimizing the temperature, baking time, and ratio of solids to glass microspheres, a floating puck is formed.

Example 4

The following mineral components are crushed and mixed with a mortar and pestle.

| Inorganic species | gms |
| --- | --- |
| Iron Oxide | 30 |
| Iron Nitrate nonahydrate | 20 |
| Calcium Oxide | 20 |
| Calcium Phosphate | 5 |
| Magnesium Carbonate | 15 |
| Zinc Oxide | 5 |

To 10 gm of the above mixture, the following trace mineral components are added with further grinding.

| Species | gms |
| --- | --- |
| Copper Sulfate | 1.2 |
| Ammonium Molybdate | 0.6 |
| Manganese Oxide | 0.1 |
| Cobalt Nitrate hexahydrate | 0.01 |
| Boric Acid | 0.002 |
| Selenium Chloride | 0.001 |
| Vanadium Chloride | 0.0001 |
| Nickel Chloride | 0.0001 |
| Chromium Chloride | 0.0001 |

To this solid powder, 300 mL of colloidal silica in water (Snowtex-N, Nissan Chemical Industries, Tokyo Japan) and 400 mL Perlite are added. The slurry is quickly mixed in a wiper-type rotary mixer and extruded as coarse gel pellets into a furnace designed with modification from the teachings of U.S. Pat. No. 4,257,799. Brief exposure to temperatures of about 1000° C. results in a glass coating on the pellets. By adjusting transit temperatures and times in the furnace, a hard, pelletized inorganic composition having a density of less than 1 $gm/cm^3$ results. The pellets readily disperse when floated on water and are sufficiently buoyant as to provide a strongly retroreflective substrate.

Similar results can be obtained through the use of blowing agents which decompose at elevated temperature (for example urea at temperatures exceeding 600° C.) without the need for Perlite or glass hollow microspheres. The resultant products contain no organic components, the blowing agent having been decomposed to inorganic components (in the case of urea, carbon dioxide and ammonia). Gas injected into molten glasses also results in floating glass "pellets", sensu lato. Methods for rapid thermal processing are favored so as to limit gaseous diffusion in the matrix during processing.

Example 5

A formulation development sequence is undertaken which results in a mineraline composition in a glass or crystalline flotational matrix that favors the growth of diatoms.

Example 6

A formulation development sequence is undertaken which results in a mineraline composition in a glass or crystalline buoyant matrix that favors the growth of coccolithophorids.

Example 7

A formulation development sequence is undertaken which results in a fractal, porous mineraline substrate in a glass or crystalline flotational matrix that favors the establishment of a complex food chain of primary producers grazers, and higher trophic levels.

Example 8

A formulation development sequence is undertaken which results in a glass or crystalline flotational composition that enhances the albedo of planetary surface bodies of water.

Example 9

In support of the development sequences of Examples 5, 6, 7, and 8, an ocean buoy of FIG. 5 or 6 is designed and anchored at a suitable field study site. Data collected in the field include insolation and reflected radiation, gross and net sequestration in sediments, primary production, and harvestable fish yields, comparing different formulations.

Also evaluated in the field are the weatherability and leaching rates of the formulations, although preliminary evaluations are typically made in stirred vessels of the sort used by the pharmaceutical industry to measure tablet dissolution.

Example 10

A modified stoneware clay is mixed as follows:

| | |
|---|---|
| Water | 28 lb |
| Fireclay: | 41 lb |
| OM4 Ball Clay: | 24 lb |
| Kaolin: | 10 lb |
| Silica Powder: | 10 lb |
| Sodium Silicate 40% (v/v): | 20 lb |
| G-200 Feldspar | 10 lb |
| Fe, Mg, Ca, Zn and trace elements | 10 lb |

The mixture is mixed with forced injection of air or $CO_2$ and extruded into a ribbon. During firing, the green ceramic ribbon is coated with a glass mixture of titanium oxide and silica dioxide or magnesium fluoride. An inorganic gas precursor such as urea is included. As a practical matter, it may be useful to include fibers for tensile strength, such as those of Kevlar® (Dupont, Richmond Va.), glass wool, carbon fibers, graphite, gypsum, or polyester. Larger structures can be made by applying the clay over a cementitious vessel composed of Sorel Cement or Portland Cement.

Example 11

Perlite floated in an inorganic algal growth medium in a Petri dish was heavily and rapidly colonized by mixed populations of algae and diatoms after inoculation with soil or pond water. This primary producer population was soon joined by grazers and heterotrophic species.

Example 12

As a full scale field demonstration, a prill [nozzle extruded] of mineral:silica glass formulation impregnated with microbubbles is released into the equatorial Pacific Ocean in an area of offshore flow from Peru, from which it disperses in a generally east to west track by the action of currents as a plume larger than the size of New Zealand. The material has a half-life of 1 year and contains iron, calcium, magnesium, zinc, and trace copper, molybdate, manganese, cobalt, borate, selenium, vanadium, and nickel, supplemented with nitrate, phosphate, and with blowgas enriched in $CO_2$. The free-flowing, buoyant prill particles are designed to promote growth of phytoplankton, increase higher trophic levels and complexity, increase sedimentary deadfall of fixed carbon, and to have sustained release properties.

Production is assumed to be 2 million metric tons annually. Cost per metric ton of raw material is on the order of $20 US FOB. Plant capacity is expected to cost US$25-50M. Energy capacity for operating the plant is on the order of 20 MW, at a cost of $50 to $100 per MWhr. These figures are based on US production of an analogous material termed in the trade, "perlite", such as is used extensively in horticulture and insulation.

If dispersed at 5 gm per meter squared, production is sufficient to cover 360,000 square kilometers of ocean. Reaching the central pacific in about 3 months, the material acts as snow or ice, reflecting incident sunlight. An increase of 0.05 in albedo is obtained. An immediate decrease in surface temperature in the plume due to the increased albedo is estimated from the Stephan-Boltzmann equation, assuming pseudo-adiabatic surface layer cooling. The calculated value is a reduction in SST of 2.9° C., based on a reduction in insolation absorbed by the ocean water of 17 Watts/m$^2$. Because ENSO events are associated with 4° C. increases in central warm pool Pacific Ocean temperatures, this 2.9° C. cooling is highly significant. A similar drop in air temperature over the affected body of water is also noted. As an immediate result: 1) an ENSO event predicted for that year is significantly reduced in intensity; 2) there is no drought in Australia that year; 3) the expected El Niño off Chile does not materialize, 4) the Humboldt current continues with offshore flow and ocean upwelling, 5) contributing indirectly to good fishing that year. No harm is done, and the material has essentially vanished in less than 3 years.

Furthermore, by increasing net sedimentary benthic export of fixed $CO_2$ to 3 gm $CO_2$/m$^2$/day in the plume, an annualized deadfall (fixed carbon to the benthos) of 275 tC/km$^2$/yr is feasible. In a plume of 360,000 km$^2$, 0.4 Gt $CO_2$ is exported below the 100 Year horizon over a year.

The cooling effect is multiplied by synergic effects. Following release, the sulfur cycle is studied. As surface mixing decreases in the plume, DMS production increases significantly, resulting in increased kumogenesis extending thousands of miles downstream, generally westerly, from the plume. A noticeable cooling of the earth that season is observed as the result of the de novo stimulation of cloud formation over the Pacific.

In this example, the rate of release of nutrients from the prill is determined by the leachable counterion content of the glass. Calcium oxide will desolubilize glass, and monovalent anions such as potassium oxide will increase it. By adjusting the ratio of divalent to monovalent cations in the glass, its solubility and rate of leaching can be controlled. The ratio of cross-sectional area to surface area is also a factor in controlling leaching. By modifying the underside of the prill in a floating matrix such as an extruded ribbon cut to suitable lengths, increased biological habitat can be obtained. Increases in primary production are also associated with increases in production of harvestable species. Buoyant SRC prill may also be made from foamed or exploded clay, such as kaolin, which is far more abundant than perlite glass.

All of the U.S. patents, U.S. patent application publications, U.S. patent applications, foreign patents, foreign patent applications and non-patent publications referred to in this specification and/or listed in the Information Data Sheets, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the specifics of the disclosure.

What is claimed is:

1. An apparatus for validating continuous sequestration of carbon below the 100-Year Horizon of an ocean and issuing a monetizable or tradeable carbon sequestration certificate having a denomination based on the mass of carbon sequestered therebelow, which comprises:
   a) a spar buoy or network of spar buoys disposed on the surface of an open ocean, each spar buoy comprising a vertically elongate hollow body having a top end with superstructure and a bottom end with ballast mass, said hollow body having an upper fixed displacement volume (V1) and a lower variable displacement volume (V2);
   b) a horizontally disposed spaceframe immersedly suspended from said spar buoy or network of spar buoys;
   c) an immersed analytical apparatus mounted on said spaceframe for measuring sedimentary deadfall as an index of flux of sequestered carbon descending below the 100-Year Horizon of said ocean;
   d) a surface boom for enclosing a surface area of said ocean associated with said spar buoy or network of spar buoys;
   e) a pump mounted in said spar buoy, said pump having a fluidic connection for drawing nutrient-rich water from below the photic zone of an ocean and discharging said nutrient-rich water from said top end onto or proximate to the surface thereof; and,
   f) a computer-implemented system operatively connected to said analytical apparatus and configured for integrating and reporting electronically a flux of sequestered carbon descending below the 100-Year Horizon per unit time or issuing one or more monetizable or tradable carbon sequestration certificates, wherein each certificate has a denomination equivalent to a validated amount of sequestered carbon as $CO_2$ in the sedimentary deadfall descended from said enclosed surface area to below the 100-Year Horizon of said ocean.

2. The apparatus of claim 1, further comprising a habitat-forming composition buoyantly disposed within a surface area defined by said spar buoy or network of spar buoys, said habitat for increasing the size and complexity of trophic levels associated therewith.

3. The apparatus of claim 2, wherein said composition comprises a slow release formulation efficacious in promoting the sedimentation of fixed $CO_2$.

4. The apparatus of claim 3, wherein the slow-release formulation comprises a silicate or a calcite.

5. The apparatus of claim 1, wherein said pump is powered by renewable energy.

6. The apparatus of claim 1, further comprising a second pump for adjusting said lower variable displacement volume (V2), whereby said top end is enabled to be submerged so as to withstand high waves.

7. The apparatus of claim 1, further comprising a data processing and communications system for registering or trading said carbon sequestration certificates in a market or through a broker, which comprises at least one computer of a network, said computer comprising one or more processors, at least one volatile memory with database, said database containing records, wherein said records include an inventory of certificates that have been registered and are available for trading and their denomination, and at least one non-volatile read-only memory containing computer readable code embodied therein for causing said computer to execute a program module comprising registering and inventorying said certificates and executing or assisting in execution of trades in said certificates.

8. The apparatus of claim 7, further comprising at least one interactive display for displaying an inventory or a record of a trade.

9. The apparatus of claim 7, wherein the system is configured for recording ask and bid prices, recording trades, and processing payments and credits.

10. The apparatus of claim 1 comprising a weather monitor instrumentation module and a radio module for reporting local marine conditions.

11. The apparatus of claim 1, wherein said superstructure comprises a pelagic aquaculture workstation.

12. The apparatus of claim 1, wherein said network of spar buoys comprises a planar array, hexagonal array, or an annular array of spar buoys.

13. The apparatus of claim 1, wherein said spar buoy or network of spar buoys are submersibly anchored to one or more retractable cables attached to the seafloor, and said spar buoy or network of spar buoys has a waterline enabled to be configured with pumps and winches.

14. The apparatus of claim 1, wherein said apparatus is not anchored and is retained in an ocean gyre by the passive circulation of currents.

15. The apparatus of claim 14, wherein said composition dispersed in said enclosed surface area is formulated to accelerate bioremediation of plastic waste in said gyre.

16. A method comprising:
   a) floating an apparatus of claim 2 in an ocean, whereby a surface area of said ocean is defined;
   b) pumping nutrient-rich water from below the photic zone of the ocean through said spar buoy and discharging said nutrient-rich water onto or proximate to the surface of the ocean;
   c) dispersing said composition in said defined surface area;
   d) measuring sedimentary deadfall data as an index of sequestered carbon flux descending from said enclosed surface area to below the 100-Year Horizon of said ocean; and,
   e) integrating sequestered carbon flux descending below the 100-Year Horizon per unit time from said surface area and issuing one or more monetizable or tradable carbon sequestration certificates, wherein each certificate has a denomination equivalent to a validated amount of sequestered carbon as $CO_2$ in the sedimentary deadfall descended from said surface area to below the 100-Year Horizon.

17. The method of claim 16, further comprising harvesting a sustainable yield of a higher trophic level biomass from said surface area of said ocean associated with said spar buoy or network of spar buoys.

18. The method of claim 16, wherein the carbon sequestration certificate comprises a $CO_2$ emission certificate, a $CO_2$ emission permit, a $CO_2$ emission credit, a carbon offset, carbon allowance, a criteria pollutant allowance, a Verified Emissions Reductions unit (VER), a Carbon Financial Instrument (CFI), a European Union Allowance (EUA), a Certified Emission Reduction unit (CER), an Emission Reduction Unit (ERU), a Voluntary Carbon Unit, a greenhouse gas emission credit, a carbon offset, or a tipping fee.

19. The apparatus of claim 1, wherein the computer-implemented system is configured to generate a certificate comprising a $CO_2$ emission certificate, a $CO_2$ emission permit, a $CO_2$ emission credit, a carbon offset, carbon allowance, a criteria pollutant allowance, a Verified Emissions Reductions unit (VER), a Carbon Financial Instrument (CFI), a European Union Allowance (EUA), a Certified Emission Reduction unit (CER), an Emission Reduction Unit (ERU), a Voluntary Carbon Unit, a greenhouse gas emission credit, a carbon offset, or a tipping fee.

* * * * *